(12) United States Patent
Ngo et al.

(10) Patent No.: US 11,197,684 B1
(45) Date of Patent: Dec. 14, 2021

(54) THROMBECTOMY DEVICE AND METHOD

(71) Applicant: Nventric Corporation, Seoul (KR)

(72) Inventors: Don Quy Ngo, Los Angeles, CA (US); Sungwoo Min, Fullerton, CA (US); Jiyoung Min, Seoul (KR)

(73) Assignee: NVENTRIC CORPORATION, Seoul (KR)

( * ) Notice: Subject to any disclaimer, the term of this patent is extended or adjusted under 35 U.S.C. 154(b) by 0 days.

(21) Appl. No.: 17/192,786

(22) Filed: Mar. 4, 2021

(51) Int. Cl.
*A61B 17/221* (2006.01)
*A61F 2/01* (2006.01)
*A61B 17/22* (2006.01)
*A61B 17/00* (2006.01)

(52) U.S. Cl.
CPC .. *A61B 17/221* (2013.01); *A61B 2017/00526* (2013.01); *A61B 2017/2212* (2013.01); *A61B 2017/22034* (2013.01); *A61B 2017/22038* (2013.01); *A61B 2017/22094* (2013.01)

(58) Field of Classification Search
CPC .......... A61B 17/221; A61B 2017/2212; A61B 2017/2215; A61B 2017/22039
See application file for complete search history.

(56) References Cited

U.S. PATENT DOCUMENTS

| | | | |
|---|---|---|---|
| 8,777,976 B2 | 7/2014 | Brady et al. | |
| 8,852,205 B2 | 10/2014 | Brady et al. | |
| 9,301,769 B2 | 4/2016 | Brady et al. | |
| 9,351,749 B2 | 5/2016 | Brady et al. | |
| 9,402,707 B2 | 8/2016 | Brady et al. | |
| 9,433,429 B2 | 9/2016 | Vale et al. | |
| 9,445,829 B2 | 9/2016 | Vale et al. | |
| 9,463,036 B2 | 10/2016 | Brady et al. | |
| 9,642,635 B2 | 5/2017 | Vale et al. | |
| 9,642,639 B2 | 5/2017 | Brady et al. | |
| 10,034,680 B2 | 7/2018 | Brady et al. | |
| 10,080,575 B2 | 9/2018 | Brady et al. | |
| 10,201,360 B2 | 2/2019 | Vale et al. | |
| 10,265,086 B2 | 4/2019 | Vale et al. | |
| 10,278,717 B2 | 5/2019 | Brady et al. | |
| 10,285,720 B2 | 5/2019 | Gilvarry et al. | |
| 10,292,722 B2 | 5/2019 | Brady et al. | |
| 10,292,723 B2 | 5/2019 | Brady et al. | |
| 10,299,811 B2 | 5/2019 | Brady et al. | |
| 10,357,265 B2 | 7/2019 | Brady et al. | |
| 10,363,054 B2 | 7/2019 | Vale et al. | |

(Continued)

*Primary Examiner* — Tuan V Nguyen
(74) *Attorney, Agent, or Firm* — Womble Bond Dickinson (US) LLP

(57) ABSTRACT

A mechanical thrombectomy device, and methods of manufacturing and using the mechanical thrombectomy device, are described. The mechanical thrombectomy device includes several clot arrestors independently mounted on a support wire. The clot arrestors have expandable frames that are eccentrically supported on the support wire. The independently and eccentrically mounted clot arrestors are arranged to allow a clot to pass into, and be captured by, one of the expandable frames. Furthermore, the independently and eccentrically mounted clot arrestors deform independently of one another such that retraction of the mechanical thrombectomy device through tortuous vasculature can stretch one clot arrestor without stretching another one of the clot arrestors to allow the clot to be retained by the unstretched clot arrestors. Other embodiments are also described and claimed.

24 Claims, 9 Drawing Sheets

(56) References Cited

U.S. PATENT DOCUMENTS

| | | |
|---|---|---|
| 10,390,850 B2 | 8/2019 | Vale et al. |
| 10,420,570 B2 | 9/2019 | Vale et al. |
| 10,441,301 B2 | 10/2019 | Vale et al. |
| 10,517,622 B2 | 12/2019 | Vale et al. |
| 10,588,648 B2 | 3/2020 | Brady et al. |
| 10,588,649 B2 | 3/2020 | Brady et al. |
| 10,610,246 B2 | 4/2020 | Brady et al. |
| 10,617,435 B2 | 4/2020 | Vale et al. |
| 10,667,833 B2 | 6/2020 | Vale et al. |
| 10,675,045 B2 | 6/2020 | Brady et al. |
| 10,682,152 B2 | 6/2020 | Vale et al. |
| 10,582,939 B2 | 7/2020 | Brady et al. |
| 10,743,894 B2 | 8/2020 | Brady et al. |
| 10,792,055 B2 | 10/2020 | Brady et al. |
| 10,792,056 B2 | 10/2020 | Vale et al. |
| 10,842,498 B2 | 11/2020 | Vale et al. |
| 2002/0161393 A1* | 10/2002 | Demond ............... A61F 2/01 606/200 |
| 2008/0167678 A1* | 7/2008 | Morsi ........... A61B 17/320725 606/200 |
| 2008/0275490 A1* | 11/2008 | Fleming ............... A61F 2/012 606/200 |
| 2013/0144326 A1* | 6/2013 | Brady ................... A61F 2/013 606/200 |
| 2013/0184739 A1 | 7/2013 | Brady et al. |
| 2014/0379023 A1 | 12/2014 | Brady et al. |
| 2015/0032121 A1* | 1/2015 | Janardhan ............... A61M 1/84 606/127 |
| 2016/0066921 A1 | 3/2016 | Seifert et al. |
| 2018/0263632 A1 | 9/2018 | Seifert et al. |
| 2018/0344338 A1 | 12/2018 | Brady et al. |
| 2019/0000492 A1 | 1/2019 | Casey et al. |
| 2019/0142442 A1 | 5/2019 | Vale et al. |
| 2019/0167287 A1 | 6/2019 | Vale et al. |
| 2019/0201014 A1 | 7/2019 | Vale et al. |
| 2019/0223893 A1 | 7/2019 | Gilvarry et al. |
| 2019/0231372 A1 | 8/2019 | Brady et al. |
| 2019/0239907 A1 | 8/2019 | Brady et al. |
| 2019/0239908 A1 | 8/2019 | Brady et al. |
| 2019/0239910 A1 | 8/2019 | Brady et al. |
| 2019/0298397 A1 | 10/2019 | Vale et al. |
| 2019/0328411 A1 | 10/2019 | Vale et al. |
| 2019/0336151 A1 | 11/2019 | Vale et al. |
| 2019/0365399 A1 | 12/2019 | Vale et al. |
| 2020/0000483 A1 | 1/2020 | Brady et al. |
| 2020/0046390 A1 | 2/2020 | Brady et al. |
| 2020/0060703 A1 | 2/2020 | Vale et al. |
| 2020/0100804 A1 | 4/2020 | Casey et al. |
| 2020/0107851 A1 | 4/2020 | McCarthy |
| 2020/0121339 A1 | 4/2020 | Brady et al. |
| 2020/0246031 A1 | 8/2020 | Vale et al. |
| 2020/0281611 A1 | 9/2020 | Kelly et al. |
| 2020/0281612 A1 | 9/2020 | Kelly et al. |
| 2020/0305900 A1 | 10/2020 | Vale et al. |
| 2020/0323615 A1 | 10/2020 | Casey et al. |
| 2020/0345904 A1 | 11/2020 | Casey et al. |
| 2020/0353205 A1 | 11/2020 | Kelly et al. |
| 2020/0353226 A1 | 11/2020 | Keating et al. |
| 2020/0353228 A1 | 11/2020 | Casey et al. |
| 2020/0353229 A1 | 11/2020 | Casey et al. |

* cited by examiner

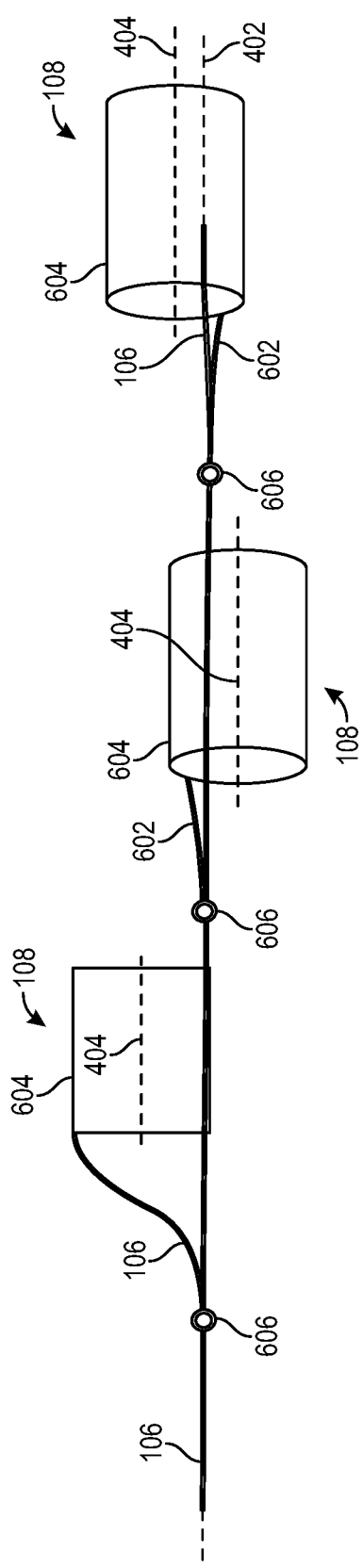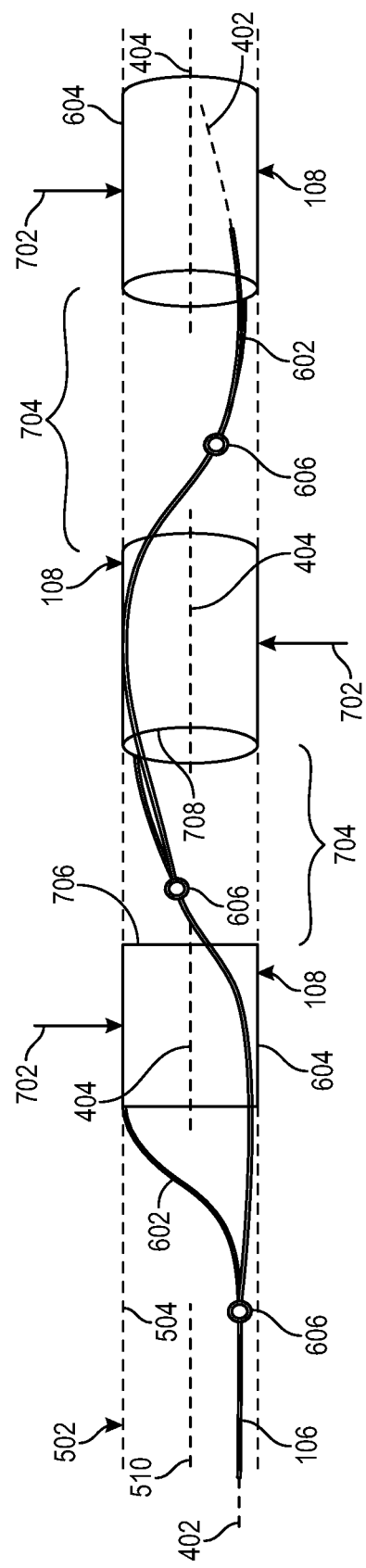
FIG. 6
FIG. 7

THROMBECTOMY DEVICE AND METHOD

BACKGROUND

Field

The present disclosure relates to mechanical thrombectomy devices used for ischemic stroke treatments. More specifically, the present disclosure relates to mechanical thrombectomy devices used for neurovascular thrombectomy procedures.

Background Information

Several classes of devices exist for salvaging the brain of patients suffering from acute ischemic stroke. Among the classes are mechanical thrombectomy devices, which are used to remove thrombi from the neurovasculature to restore perfusion through an initially occluded artery. Mechanical thrombectomy devices that have been cleared for such use include coil retrievers, aspiration devices, and more recently, stent retriever devices.

Existing stent retriever devices are essentially self-expanding stents that can be deployed within a thrombus to push the thrombus aside and/or entangle the thrombus within struts of the stent. After mechanically integrating with the thrombus, the stent and thrombus can be withdrawn into a delivery catheter and removed from the patient. Important factors in the usability and performance of stent retriever devices include their visibility under fluoroscopy, their ability to capture or engage a clot, and their ability to retain the captured or engaged clot as the device is retracted through tortuous vasculature. Shortcomings in these factors can extend procedural times and reduce clinical success rates.

SUMMARY

Existing stent retriever devices provide suboptimal visibility, clot engagement, and/or clot retention. Most stent retriever devices today are not easily visualized under fluoroscopy during a procedure because their structures are insufficiently radiopaque. Furthermore, most stent retriever devices today utilize a unitary stent body that hinders clot capture and engagement. For example, the unitary stent body can roll over and pass by a hard clot, thereby bouncing off of the clot rather than engaging or capturing the clot. Furthermore, the unitary stent body can stretch over its entire length when pulled around a bend in a vasculature, causing a captured clot to become disengaged and lost as the stent body is pulled around the bend.

A mechanical thrombectomy device is described below, which addresses the shortcomings of existing stent retriever devices described above. In an embodiment, the mechanical thrombectomy device includes several clot arrestors independently supported on a support wire. For example, the support wire can have a distal segment that has a smaller diameter, or is otherwise less stiff, than a proximal segment, and the clot arrestors can be mounted on the distal segment. More particularly, each clot arrestor can include an expandable frame and a stem, and the stem can couple the expandable frame to the support wire at a joint. The joint can be a mechanical joint, such as a radiopaque marker band crimped around the support wire and the stem. Thus, the joints can be visible under fluoroscopy. Furthermore, the clot arrestors can be independently supported by the support wire at respective joints that are spaced longitudinally along the support wire. As such, when a deforming load is applied to one of the expandable frames, the deforming load is not transmitted to another one of the expandable frames. This can allow, for example, one expandable frame to stretch and lose apposition with a vessel wall when being pulled around a bend in a blood vessel, without causing the other expandable frames to stretch and lose apposition with the vessel wall. The mechanical thrombectomy device can therefore more effectively capture and retrieve clots from tortuous anatomies.

The expandable frames of the several clot arrestors can be eccentrically supported on the support wire. For example, the expandable frames can be arranged such that arrestor axes of the expandable frames are not aligned with a wire axis of the support wire when the clot arrestors are deployed in free space. When the clot arrestors are deployed in the blood vessel, however, the expandable frames can appose the vessel wall and be forced into a concentric relationship with the vessel wall. Accordingly, the arrestor axes can align with the central axis of the blood vessel, which can force the support wire radially outward toward the vessel wall. The support wire can therefore extend through the expandable frames offset from the central axis of the blood vessel, e.g., spiraling along the vessel wall, leaving a lumen of the blood vessel and interior channels of the expandable frames open to receive a clot. The mechanical thrombectomy device can therefore more effectively capture hard clots that will roll into the interior channel to be captured rather than rolling between the device and the vessel wall to be lost downstream.

The expandable frames of the several clot arrestors can be non-concentrically supported on the support wire. For example, the expandable frames can be arranged such that arrestor axes of the expandable frames are not aligned with each other when the clot arrestors are deployed in free space. When the clot arrestors are deployed in the blood vessel, however, the expandable frames can appose the vessel wall and be forced into a concentric relationship with each other. The expandable frames can resiliently press outward to attempt to return to the undeformed, free state. The outward pressure from the resilient frames can be applied to the vessel wall in different transverse directions, since the expandable frames are non-concentric in the free state. Accordingly, the non-concentric expandable frames can increase a distributed radial force around the vessel wall, which may aid clot capture as the device is retracted through the blood vessel.

Capture of clots can be further enhanced by features of the mechanical thrombectomy device, such as a filter disposed at a distal end of the device, or the openings between adjacent independently-supported clot arrestors. The filter can be formed from a self-expandable mesh that allows blood to pass distally, but captures clots. The openings can be adjusted by changing the spacing of the joints, the expandable frame geometry, or other variables to provide ports that hard or soft clots can pass through to be captured within the interior channel of the mechanical thrombectomy device. A method of manufacturing the mechanical thrombectomy device, and a method of using the mechanical thrombectomy device to remove a clot from a blood vessel are also described below.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6 is a side pictorial view of several clot arrestors deployed in free space, in accordance with an embodiment;

FIG. 7 is a side pictorial view of several clot arrestors deployed in a straight blood vessel, in accordance with an embodiment;

DETAILED DESCRIPTION

Figure 1:
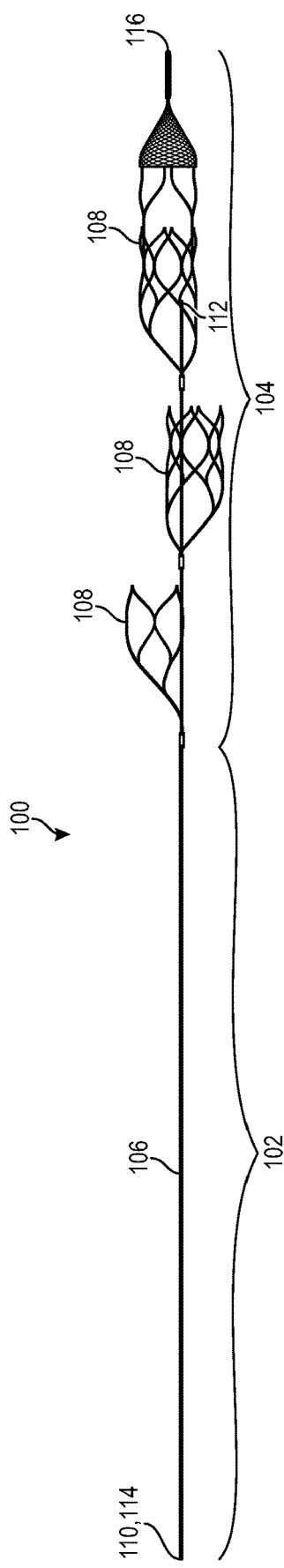
FIG. 1 is a plan view of a mechanical thrombectomy device, in accordance with an embodiment.

Embodiments describe a mechanical thrombectomy device having clot arrestors independently and eccentrically mounted on a support wire. The mechanical thrombectomy device can be used to treat acute ischemic stroke. The mechanical thrombectomy device may, however be used in other applications, such as removal of clots from other vessels.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a support wire or clot arrestor. Similarly, "proximal" may indicate a second direction opposite to the first direction. Such terms are provided to establish relative frames of reference, however, and are not intended to limit the use or orientation of a mechanical thrombectomy device to a specific configuration described in the various embodiments below.

In an aspect, a mechanical thrombectomy device includes several clot arrestors mounted on a support wire. The clot arrestors are independently mounted. More particularly, each clot arrestor includes an expandable frame that is attached to the support wire independently from the expandable frames of the other clot arrestors. Whereas competitive devices stretch significantly when pulled around a bend in a tortuous vessel, the segmented configuration of the mechanical thrombectomy device allows the clot arrestors to act independently of each other. Accordingly, stretching one clot arrestor does not cause another clot arrestor to stretch significantly. As a result, when the mechanical thrombectomy device is retracted around a bend, even though the clot arrestor at the bend may stretch and lose apposition with the vessel wall, the clot arrestors distal and proximal to the bend remain un-stretched and apposed to the vessel wall. Accordingly, should the clot arrestor at the bend lose engagement with the clot, the clot can move into and be captured and retained by the other clot arrestors that appose the vessel wall.

In an aspect, the clot arrestors of the mechanical thrombectomy device are eccentrically supported on the support wire. When the clot arrestors are deployed into a blood vessel and become concentrically arranged within the blood vessel, the support wire can be pushed off center and therefore may extend through the expandable frames of clot arrestors offset from a central axis of the blood vessel. The eccentric configuration of the expandable frames and the non-central location of the support wire can allow a clot to pass into and be captured by the expandable frames. Whereas unitary stent bodies of existing stent retriever devices may not allow capture of a clot (and instead allow the clot to roll between the body and the vessel wall while the device is retracted), the segmented clot arrestors of the mechanical thrombectomy device allow the clot to enter into a gap between the clot arrestors and therefore be captured by the clot arrestors.

In an aspect, the clot arrestors of the mechanical thrombectomy device are attached to the support wire by joints that are highly visible under fluoroscopy. For example, each joint that connects a clot arrestor to the support wire can include a radiopaque marker. The radiopaque markers define specific locations along the support wire relative to the clot arrestors. Accordingly, the radiopaque markers promote visibility of the device, and provide cues to an operator to understand where a clot is located relative to the clot arrestors.

Referring to FIG. 1, a plan view of a mechanical thrombectomy device is shown in accordance with an embodiment. A mechanical thrombectomy device 100 is an endovascular tool that can be used to treat acute ischemic stroke. The mechanical thrombectomy device 100 includes a proximal control region 102 used by an operator to advance, retract, and rotate a distal working region 104 of the device. More particularly, the mechanical thrombectomy device 100 includes a support wire 106 that the operator can push to advance the distal working region 104, pull to retract the distal working region 104, or twist to rotate the distal working region 104. The mechanical thrombectomy device 100 can include several clot arrestors 108 that can be advanced through and deployed from a microcatheter into a target anatomy. The clot arrestors 108, when deployed within the target anatomy, can capture, catch, engage, or mechanically integrate with a clot. The arrested clot can be retrieved from a patient by pulling the support wire 106 to retract the clot arrestors 108 and the clot from the vasculature.

In an embodiment, the support wire 106 includes a proximal wire end 110 and a distal wire end 112. The support wire 106 can extend longitudinally from the proximal wire end 110 to the distal wire end 112 along a wire axis. The support wire 106 can be a flexible elongated wire formed from a resilient material, such as stainless steel or a superelastic nickel titanium alloy, and thus, the wire axis may have one or more straight or curvilinear segments between the proximal wire end 110 and the distal wire end 112. A length of the support wire 106 may be less than an overall length of the mechanical thrombectomy device 100. For example, the distal wire end 112 may be located distal to at least one of the clot arrestors 108, and proximal to a distal end of at least one of the clot arrestors 108. Accordingly, a distance from the proximal wire end 110 (at a proximal device end 114) to the distal wire end 112 may be less than a distance from the proximal wire end 110 to a distal device end 116.

Figure 2:
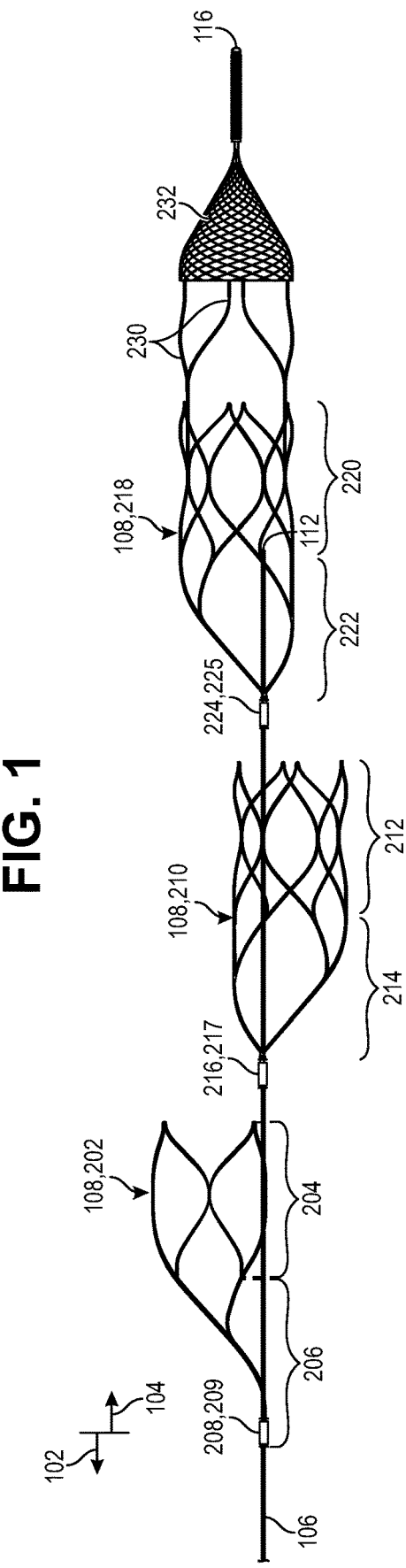
FIG. 2 is a plan view of a distal portion of a mechanical thrombectomy device having several clot arrestors, in accordance with an embodiment.

Referring to FIG. 2, a plan view of a distal portion of a mechanical thrombectomy device having several clot arrestors is shown in accordance with an embodiment. The clot arrestors are independently mounted on the support wire 106. More particularly, each clot arrestor 108 includes a respective expandable frame, and the respective expandable frames of the clot arrestors 108 are connected to the support wire 106 at respective locations. For example, a first clot arrestor 202 has a first expandable frame 204 and a first stem 206 that connects the first expandable frame 204 to the support wire 106 at a first joint 208. The first joint 208 can be at a first location 209 along the support wire 106. A second clot arrestor 210 has a second expandable frame 212 and a second stem 214 that connects the second expandable frame 212 to the support wire 106 at a second joint 216. The second joint 216 can be at a second location 217 along the support wire 106. The mechanical thrombectomy device 100 may have more than two clot arrestors 108. For example, a third clot arrestor 218 has a third expandable frame 220 and a third stem 222 that connects the third expandable frame 220 to the support wire 106 at a third joint 224. The third joint 224 can be at a third location 225 along the support wire 106. The attachment points of the respective clot arrestors 108 can be longitudinally separated along the support wire 106. For example, the first location 209, the second location 217, and the third location 225 can be at different longitudinal locations on the support wire 106. Accordingly, the expandable frames of the clot arrestors 108 can be arranged in series in the longitudinal direction, and each expandable frame can be independently supported on the support wire 106 relative to the other expandable frames.

The sequentially arranged clot arrestors 108 may have identical or different structures. For example, in the embodiment shown in FIG. 2, the most proximal clot arrestor, i.e., the first clot arrestor 202, and the middle clot arrestor, i.e., the second clot arrestor 210, are identical in that the stems and joints of those expandable frames have the same geometries. By contrast, the distalmost clot arrestor 108, i.e., the third clot arrestor 218, can have a geometry that differs from the first clot arrestor 202 and the second clot arrestor 210. Some of these geometrical differences are described below, but it will be appreciated that one difference can be the presence of one or more struts 230 extending distally from an expandable frame to support a filter 232 at the distal device end 116. Accordingly, the independently supported clot arrestors 108 can be sized and shaped to provide respective degrees of clot engagement, clot capture, flexibility, or any other performance attribute.

Figure 3:
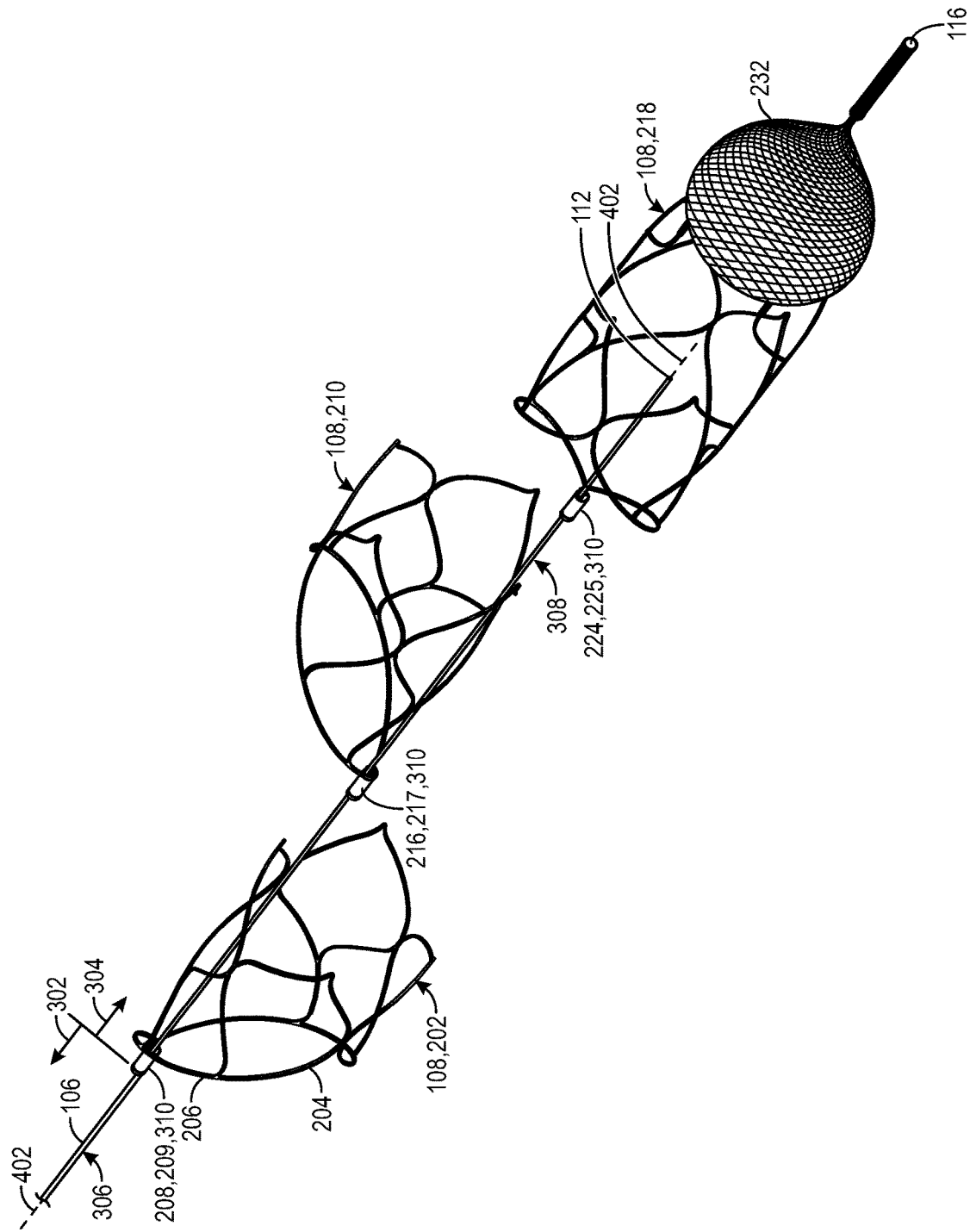
FIG. 3 is a perspective view of a distal portion of a mechanical thrombectomy device having several clot arrestors, in accordance with an embodiment.

Referring to FIG. 3, a perspective view of a distal portion of a mechanical thrombectomy device having several clot arrestors is shown in accordance with an embodiment. The support wire 106 that supports the clot arrestors 108 may have a proximal segment 302 and a distal segment 304. The proximal segment 302 may extend over the proximal control region 102, proximal to the clot arrestors 108, and the distal segment 304 may extend within the distal working region 104, through one or more of clot arrestors 108.

The support wire 106 segments can be adapted to their purpose. For example, the proximal segment 302 may function primarily to transfer axial and rotational loads from the operator to the distal working region 104. Accordingly, the proximal segment 302 of the support wire 106 may have a proximal diameter 306 suited to those functions. By way of example, the proximal diameter 306 can be in a range of 0.010-inch to 0.020-inch, e.g., 0.018-inch. By contrast, rather than functioning primarily to transmit control forces, the distal segment 304 may function primarily as a support for the clot arrestors 108. As such, the distal segment 304 can have a distal diameter 308 that is less than the proximal diameter 306. For example, the distal diameter 308 can be in a range of 0.004-inch to 0.010-inch, e.g., 0.0045-inch. Accordingly, the proximal segment 302 of the support wire 106 can have a larger diameter than the distal segment 304 of the support wire 106. The smaller diameter of the distal segment 304 may serve several purposes. First, the smaller diameter can impart flexibility to the distal segment 304 of the support wire 106, allowing it to undulate and spiral along an inner dimension of the target anatomy and clot arrestors 108, as described below. Second, the distal segment 304 extends through the clot arrestors 108, and thus, the smaller diameter allows or a smaller packing ratio when the mechanical thrombectomy device 100 is being advanced through a micro catheter. The smaller packing ratio can allow the device to be delivered more easily through the micro catheter to the target anatomy.

The structure of the support wire 106 described above may be achieved by a single wire. For example, a single wire can be ground or otherwise tapered at discrete locations between the proximal wire end 110 and the distal wire end 112 to form the proximal segment 302 and the distal segment 304. By way of example, a single wire may be 0.018-inch at the proximal wire end 110, and can taper distally over its length to have diameters of 0.010-inch, 0.006-inch, and 0.0045-inch at different locations along the wire length. The taper can be uniform, or introduced at discrete locations to form several wire segments having respective diameters.

In an embodiment, the support wire 106 is made from several wire segments joined together. For example, the proximal segment 302 may be a first wire having a distal end at the first location 209. Similarly, the support wire 106 can include a second wire having a proximal end at the first location 209. The first wire can have a larger diameter than the second wire, as described above. The wire segments can be joined together by a joint. For example, the first joint 208, which attaches the first clot arrestor 202 to the support wire 106, can also join the ends of the several wire segments to form a unitary support wire 106.

Each of the joints of the mechanical thrombectomy device 100 can be formed using a mechanical, thermal, or adhesive bond. For example, the first joint 208 can include a marker band that is mechanically crimped around the support wire 106 and the first stem 206 of the first clot arrestor 202 to attach the clot arrestor to the support wire 106. The marker band can be a tubular sleeve formed from platinum-iridium, stainless steel, gold, tungsten, or another radiopaque material. Accordingly, the marker band can provide a radiopaque marker 310. The first stem 206 can include a tail portion that is placed inside of the marker band adjacent to the support wire 106. When the marker band is crimped, it can squeeze the support wire 106 and stem to secure the clot arrestor to the support wire 106. In an embodiment, an adhesive may be added to further secure the marker band, the clot arrestor, and the support wire 106 to each other to form the first joint 208.

The joints may be formed in alternative manners. For example, any of the joints between the clot arrestors and the support wire 106 can be formed using a laser weld, solder, or brazed joint. The mechanical, thermal, or adhesive joints may provide a degree of radiopacity, and furthermore, may secure the radiopaque marker 310 to the support wire 106. For example, a tungsten rod may be bonded to the support wire 106 at the first location 209. Accordingly, the mechanical thrombectomy device 100 includes radiopaque marker(s) at the joint(s) along the support wire 106.

The radiopaque marker(s) make the device easier to visualize under fluoroscopy. The locations of the joints and radiopaque markers 310 can be used as cues to an operator to understand relative placement between the clot arrestors and clots within the target anatomy. For example, the radiopaque marker 310 at the first joint 208 can be proximal to the first expandable frame 204, and thus, the operator can retract the mechanical thrombectomy device 100 to retract the first joint 208 past a clot to allow the clot to advance into an interior of the first expandable frame 204. Similarly, another radiopaque marker 310 can be located at the second joint 216 at the second location 217 along the support wire 106. Thus, the operator can retract the mechanical thrombectomy device 100 to retract the second joint 216 past the clot to allow the clot to advance into an interior of the second expandable frame 212. Likewise, another radiopaque marker 310 can be located at the third joint 224 at the third location 225 along the support wire 106. Thus, the operator can retract the mechanical thrombectomy device 100 to retract the third joint 224 past the clot to allow the clot to advance into an interior of the third expandable frame 220.

The positioning of the radiopaque markers 310 proximal to the interiors of the respective expandable frames can provide several benefits. First, as described above, the location provide clear feedback to the operator of the relative location between a clot that is longitudinally aligned with the marker and the interior of the respective expandable frames. Second, by locating the marker bands proximal to the expandable frames, rather than longitudinally coincident with the expandable frames, the frames can be reduced to an unexpanded state at locations distal to the radiopaque markers 310, and thus, without enclosing the markers. More particularly, the radiopaque markers 310 do not add to a crimped diameter of the expandable frames because the joints are proximal to the expandable frames. As a result, the relative location of the markers and the expandable frames benefits a packing ratio (smaller unexpanded profile) of the mechanical thrombectomy device 100 and contributes to improved delivery of the device through a microcatheter.

Figure 4:
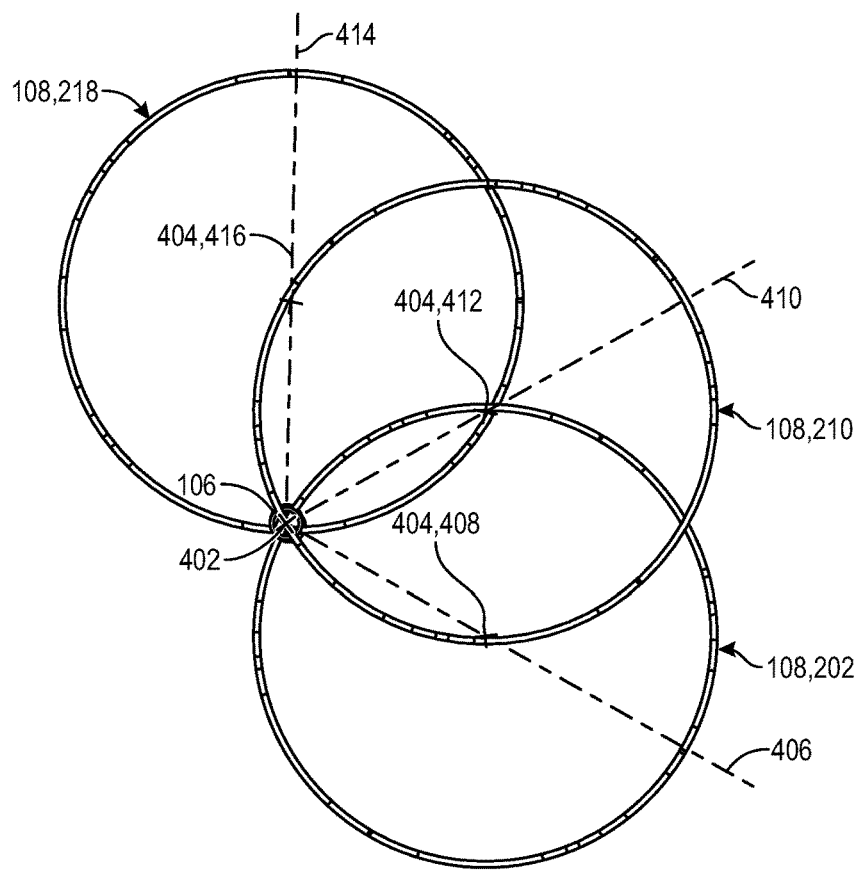
FIG. 4 is an end view of several clot arrestors deployed in free space, in accordance with an embodiment.

Referring to FIG. 4, an end view of several clot arrestors deployed in free space is shown in accordance with an embodiment. Each of the clot arrestors 108, which are independently mounted on the support wire 106, have expandable frames that are eccentrically supported on the support wire. The support wire 106 includes a wire axis 402 extending longitudinally through the support wire body. As described above, the wire axis 402 may have linear and curvilinear segments because the support wires is flexible. For modeling purposes, however, the wire axis 402 may be shown as linear (FIG. 3), and thus, is represented as a single point within the cross-sectional view of FIG. 4.

Each clot arrestor 108 can have an arrestor axis 404 that is radially offset from the wire axis 402. As described below, the clot arrestors 108 may be formed by laser-cutting a three-dimensional expandable structure from a cylindrical tube, and thus, the expandable frames of the clot arrestors 108 can have circular cross-sectional profiles, as shown in FIG. 4. The centers of these profiles can define the respective arrestor axes 404, which extend longitudinally through the clot arrestors 108. Given that the arrestor axes 404 are radially spaced from the wire axis 402, the clot arrestors 108 are eccentrically supported on the support wire 106. More particularly, the stems of the clot arrestors 108 can attach to the support wire 106 at the wire axis 402, but the expandable frames are eccentrically supported about the support wire 106.

In an embodiment, the eccentrically supported expandable frames are radially oriented about the wire axis 402. Each clot arrestor 108 can have a respective radial plane that contains the wire axis 402 and a respective arrestor axis 404. For example, a first radial plane 406 can extend radially from the wire axis 402 through a first arrestor axis 408 of the first clot arrestor 202. Similarly, a second radial plane 410 can extend radially from the wire axis 402 through a second arrestor axis 412 of the second clot arrestor 210, and a third radial plane 414 can extend radially from the wire axis 402 through a third arrestor axis 416 of the third clot arrestor 218. The radial planes can be angularly offset from each other about the support wire 106. For example, the radial planes can radiate in different directions from the wire axis 402 such that the expandable frames are non-concentrically supported on the support wire 106 relative to each other. The non-concentric distribution of the expandable frames is evident from the arrestor axes being non-coincident when viewed in the distal direction.

The radial planes of the clot arrestors 108 may be distributed about the support wire 106 uniformly or non-uniformly. In the embodiment shown in FIG. 4, the radial planes are non-uniformly distributed about the support wire 106. More particularly, an angle between the first radial plane 406 and the second radial plane 410 in a counter-clockwise direction is approximately 60°, an angle between the second radial plane 410 and the third radial plane 414 in the counterclockwise direction is approximately 60°, and an angle between the third radial plane 414 and the first radial plane 406 in the counterclockwise direction is approximately 240°. Thus, the angles between adjacent clot arrestors 108 are not equal, and the clot arrestors 108 are not uniformly oriented about the support wire 106. By contrast, the radial planes may be uniformly distributed when the angles between all adjacent clot arrestors 108 are equal. In the generalized case, the angle between radial planes is 360° divided by the number of clot arrestors 108. For example, in the case of three clot arrestors 108, the expandable frames are uniformly distributed about the support wire 106 when the angles between the first plane, the second plane, and the third plane are 120°. It will be appreciated then, that the non-uniform distribution is shown by way of example, and that the radial planes may be uniformly distributed about the support wire 106 when the angles between the radial planes are equal.

Figure 5:
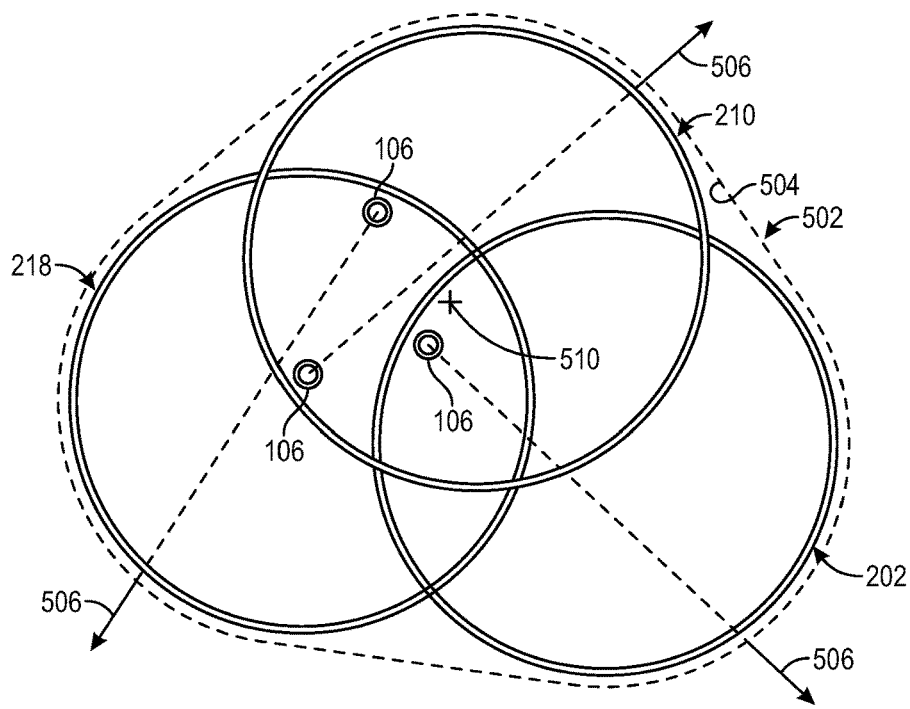
FIG. 5 is an end view of several clot arrestors deployed in a blood vessel, in accordance with an embodiment.

Referring to FIG. 5, an end view of several clot arrestors deployed in a blood vessel is shown in accordance with an embodiment. The description of eccentrically supported expandable frames provided above is made in reference to FIG. 4, which shows the clot arrestors 108 having non-coincident arrestor axes when the distal working region 104 is expanded in free space, e.g., in a naturally expanded state with no external forces being applied to the expandable frames. FIG. 5 illustrates the effect of deploying the independently and eccentrically supported clot arrestors 108 into a blood vessel 502.

When the non-concentrically supported expandable frames are constrained by a vessel wall 504 of the blood vessel 502, the vessel wall 504 will push radially inward against the expandable frames to drive the clot arrestors 108 toward a concentrically supported orientation. More particularly, given that the radial strength of the vessel wall 504 is greater than the stiffness of the distal segment 304 of the support wire 106, the support wire 106 will flex to allow the eccentrically supported expandable frames to tend toward a concentric configuration. In the illustrated example, the expandable frames are not completely concentric. This could be the case in practice, because the resilience of the support wire 106 will act on each clot arrestor 108 individually, as a result of their independently supported configuration, to push the clot arrestors 108 in different directions relative to the wire axis 402. Accordingly, in the exaggerated illustration of FIG. 5, when the plurality of clot arrestors 108 are deployed in the blood vessel 502, the expandable frames press against the vessel wall 504 in different transverse directions, as shown by force vectors 506.

Notably, the cross-sections of the first clot arrestor 202, the second clot arrestor 210, and the third clot arrestor 218 shown in FIG. 5 are actually at different longitudinal locations that are overlaid on each other. Accordingly, the cross-sections of the support wire 106 shown in FIG. 5 are at different longitudinal locations relative to each other. This realization illustrates that deployment of the clot arrestors 108 into a confining space, such as the blood vessel 502, force the support wire 106 into a non-linear shape in which the support wire 106 is not centrally located within the space. More particularly, when the clot arrestors 108 are deployed in the blood vessel 502 with the expandable frames apposed to the vessel wall 504, the support wire 106 extends through one or more of the expandable frames offset from a central axis 510 of the blood vessel 502. This result of the independently and eccentrically supported clot arrestor 108 configuration is described further below.

Referring to FIG. 6, a side pictorial view of several clot arrestors deployed in free space is shown in accordance with an embodiment. As described above, each clot arrestor 108 includes a respective stem 602 coupling a respective expandable frame 604 to the support wire 106 at a respective joint 606. The stem 602, expandable frame 604, and joints 606 can be individually labeled, e.g., first, second, and third, as described above, however, for the purposes of FIGS. 6-7 those component features are labeled generally. In the natural state, the support wire 106 can be linearly arranged, extending through one or more of the expandable frames 604. For example, the support wire 106 can extend fully through the proximal and medial expandable frames 604, and can terminate proximal to a distal end of the distal expandable frame 604. The joints 606 are spaced longitudinally along the support wire 106 and the stems 602 are separate from each other such that the expandable frames 604 are independently supported on the support wire 106. Furthermore, the expandable frames 604 are eccentrically supported on the support wire 106, as evidenced by the arrestor axes 404 being radially offset (vertically offset in the side view) from the wire axis 402.

Referring to FIG. 7, a side pictorial view of several clot arrestors deployed in a straight blood vessel is shown in accordance with an embodiment. When the distal working region 104 is deployed in the blood vessel 502, the vessel wall 504 applies a deforming load 702 to the clot arrestors 108. In this case, the deforming load 702 is a radial load, driving the arrestor axes into alignment in the radial direction. The deforming load 702 may also be an axial load (FIG. 13) that causes stretching of one or more of the expandable frames 604. In any case, as a result of the clot arrestors 108 being independently supported at the longitudinally spaced joints 606, the deforming load 702 applied to one of the expandable frames 604 is not transmitted to another one of the expandable frames 604. Rather, the expandable frames 604 are deflected independently of each other. In the illustration, this is shown as the proximal and distal expandable frames 604 being driven downward while the medial expandable frame 604 is driven upward. The independent movement of the expandable frames 604 brings the arrestor axes 404 into alignment.

As the expandable frames 604 align within the vessel, the support wire 106 is deflected into a non-linear shape. More particularly, the proximal segment 302 of the support wire 106 may remain linear, e.g., straight, but given that the arrestor axes 404 are eccentrically located with respect to the wire axis 402, as the arrestor axes 404 become more central, e.g., aligned with the central axis 510 of the blood vessel 502, the distal segment 304 of the support wire 106 supporting the expandable frames 604 may become non-linear, e.g., curved. More particularly, the wire axis 402 can become off-center, e.g., forced radially outward toward the vessel wall 504, and the support wire 106 may therefore take on a curvilinear shape that is different than the linear shape of the proximal segment 302.

In an embodiment, the support wire 106 extends through each clot arrestor 108 along an interior wall of the respective expandable frame 604. For example, as shown in FIG. 5, the support wire 106 within each expandable frame 604 is located along the interior wall of the expandable frame 604, circumferentially offset from the location that the primary force vector 506 is applied to the vessel wall 504. The support wire 106 can undulate along the vessel wall 504. In the side view of FIG. 7, this is evident from the curving path that the support wire 106 takes upward and downward in the longitudinal direction. The undulating path has peaks and valleys at which the support wire 106 is forced against the vessel wall 504 by the deforming loads 702. The peaks and valleys can coincide with the interior channel of the expandable frames 604, e.g., the support wire 106 can have a peak or a valley at an interior wall of the expandable frames 604. In an embodiment, the support wire 106 presses against the interior wall of the expandable frame 604 when it is forced away from the central axis 510 of the blood vessel 502.

In three dimensions, the undulating path of the support wire 106 may be a spiraling path. More particularly, given that the clot arrestors 108 are non-concentrically arranged about the wire axis 402, as the deforming loads 702 move the expandable frames 604 independently in different directions to force them into alignment with each other and the vessel lumen, the connections to the support wire 106, e.g., the respective joints 606, will be forced in different directions as well. This can cause the support wire 106 at one joint 606 to be forced against the blood vessel 502 at a first radial location, e.g., a zero-degree location, another joint 606 to be forced against the blood vessel 502 at a second radial location, e.g., a 120-degree location, and another joint 606 to be forced against the blood vessel 502 at a third radial location, e.g., a 240-degree location. As the support wire 106 extends longitudinally through the joints 606 at each of these radial locations, it can take on a spiraling configuration. More particularly, the support wire 106 can spiral along the vessel wall 504 when the expandable frames 604 and the respective joints 606 are apposed to the vessel wall 504. Accordingly, it will be appreciated that the support wire 106 can undulate distally making contact with the vessel wall 504 at one or more peaks or valleys, and that the support wire 106 can spiral distally making contact with the vessel wall 504 consistently over the length of the distal segment 304 of the support wire 106.

The undulating or spiraling support wire 106 provides several performance benefits. First, the offset of the support wire 106 from the vessel wall 504 causes the expandable frames 604 to press against the vessel with force vectors 506 in different directions. The support wire 106 provides a reaction load to the deforming load 702 applied to the expandable frames 604 by the vessel wall 504, and this reaction load is experienced by the vessel wall 504 as the force vectors 506. When the clot arrestors 108 are deployed in the blood vessel 502, the support wire 106 is forced away from the central axis 510 of the blood vessel 502 in different directions, and thus, the reactive loads are directed opposite to those different directions. Accordingly, the expandable frames 604 can provide a higher radial force to the vessel wall 504 when deployed in the vessel because the support wire 106 applies the force vectors 506 that press against the vessel wall 504.

Another benefit of the undulating or spiraling support wire 106 is the clearance that it provides for the capture of thrombus. When the clot arrestors 108 are deployed in the blood vessel 502, the support wire 106 is offset to the circumference of the expandable frame 604 and the blood vessel 502, which allows the central lumen, e.g., the interior channel of the expandable frames 604, to remain fully open to the passage of a clot. Still referring to FIG. 7, when the expandable frames 604 are expanded and apposed to the vessel wall 504, the support wire 106 runs along the vessel wall 504 at different circumferential locations in each expandable frame 604. A gap 704 can exist between adjacent expandable frames 604, and that gap can provide an opening through which a clot can enter into a central lumen of the mechanical thrombectomy device 100. The central lumen can be the volume that is radially inward from the vessel wall 504 and the interior wall of the expandable frame 604. It will be appreciated that a centrally located support wire 106, e.g., a support wire 106 that is aligned with a central axis 510 of the blood vessel 502, could prevent entry of the clot into the central lumen by deflecting the clot radially outward. The deflected clot could then roll between an outer surface of the expandable frames 604 and the vessel wall 504, and not be captured. By contrast, the circumferentially offset support wire 106 leaves the central lumen unblocked, and maximizes the volume in the central lumen to receive the clot. The clot then, rather than being deflected outward, is able to move fully into the central lumen to be captured by the expandable frames 604 as they are retracted through the blood vessel 502.

In addition to having a circumferentially offset support wire 106 to clear the central lumen of the device to receive clots, the gaps 704 between expandable frames 604 can also be controlled to enhance clot capture. More particularly, the openings between a distal frame end 706 of one expandable frame 604 and a proximal frame end 708 of an adjacent expandable frame 604 act as channels or ports through which clots can enter the central lumen of the device. The gaps 704 may be sized to ensure that clots, e.g., hard clots that roll between the expandable frames 604 and the vessel wall 504, will enter the gaps 704 when they become longitudinally aligned with the gaps 704. The distance between the distal frame end 706 of one expandable frame 604 and the proximal frame end 708 of the adjacent expandable frame 604 can be in a range of 10-20 mm, e.g., 15 mm, to accommodate most hard clots. It will be appreciated that the gap 704 may have a different length in the longitudinal direction, however, depending on the range of clot sizes intended for capture.

In an embodiment, the gap 704 between one pair of expandable frames 604 may be different than the gap 704 between another pair of expandable frames 604, in size or shape. For example, the length of the gap 704 between the proximalmost and medial expandable frames 604 of FIG. 7 may be different, e.g., less than, the length of the gap 704 between the medial and distalmost expandable frames 604 of FIG. 7. Similarly, the structures of the expandable frames 604 may have different geometries such that the gap 704 between the proximalmost and medial expandable frames 604 of FIG. 7 is shaped differently than the gap 704 between the medial and distalmost expandable frames 604 of FIG. 7. The variation in gap length and/or shape can provide for the openings to be more or less accommodative to different clot types. For example, a shorter and wider proximal opening may be more accommodative to capturing hard clots and a longer and narrower distal opening may be more accommodative to capturing soft clots.

Figure 8:
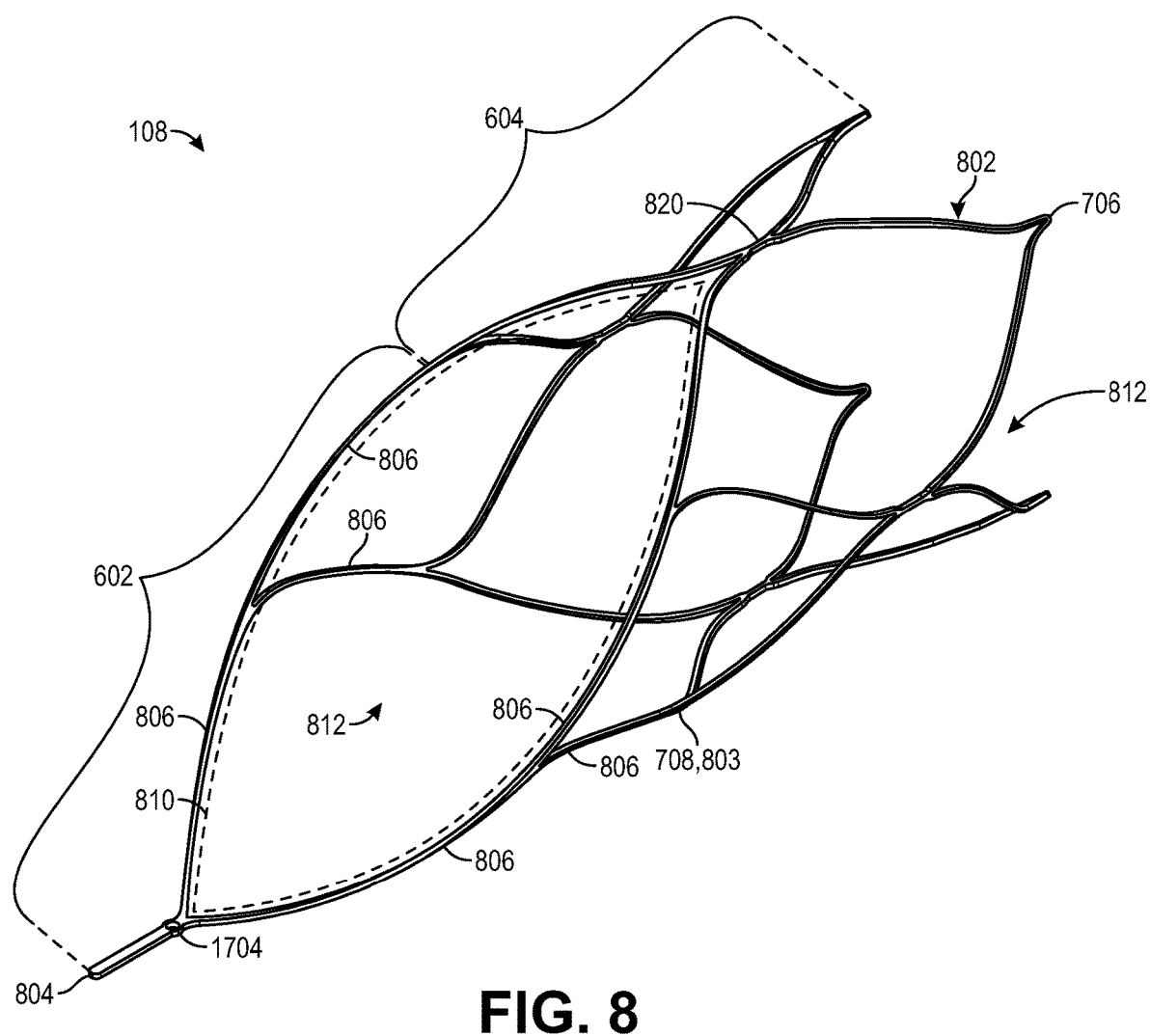
FIG. 8 is a perspective view of a clot arrestor, in accordance with an embodiment.

Referring to FIG. 8, a perspective view of a clot arrestor is shown in accordance with an embodiment. As described above, each clot arrestor 108 can have expandable frame and stem portions. The expandable frame portion 604 includes the distal frame end 706 and the proximal frame end 708. The frame ends can define openings into an interior channel 812 of the expandable frame 604, e.g., a proximal opening into a cylindrical interior of the expandable frame 604 and a distal opening into the cylindrical interior. The expandable frame 604 can include at least one ring of frame cells 802. The ring of frame cells 802 can be configured to expand and collapse. Geometrically, the expandable frame 604 can be similar to a stent. For example, the ring of frame cells 802 can include two or more cells linked to each other in a circumferential direction to form a cylindrical expandable structure having an "open" or "closed" cell pattern. The cell pattern includes one or more slots, struts, or links 820 to form an expandable structure having proximal and/or distal opening to arrest a clot. As with stents, the clot arrestor 108 can be formed by laser-cutting the cell pattern from metal tubing. For example, the expandable frame 604 can be a self-expanding structure formed from a shape memory alloy, e.g., nickel titanium tubing. Unlike stents, however, the radial force requirements of the expandable frame 604 may be secondary to the structure shape, which should accommodate clot capture rather than act as a scaffold to prop open an atherosclerotic lesion.

Also unlike stent scaffolds, the clot arrestor 108 can include the stem 602 extending proximally from the expandable frame 604. More particularly, the stem 602 can extend proximally from a proximal ring end 803 of the ring of frame cells 802 (at the proximal frame end 708) to a proximal stem end 804. Just as the distal frame end 706 can define a distalmost location or edge of the clot arrestor 108, so can the proximal stem end 804 define a proximalmost location of the clot arrestor 108. Neither the distalmost location nor the proximalmost location of the clot arrestor 108 is directly connected to an adjacent clot arrestor, and thus, the clot arrestor 108 is an independent body freely suspended on the support wire 106.

In an embodiment, the stem 602 includes one or more branches extending from the proximal stem end 804 to the proximal frame end 708. The stem 602 could be a single, straight wire segment extending proximally from the expandable frame 604 to the joint 606 at the support wire 106, as modeled in FIGS. 6-7. In an embodiment, however, the stem 602 includes several branches that extend between the joint 606 at the proximal stem end 804 and the proximal ring end 803 of the ring of frame cells 802. The branches can act as tails that trail the expandable frame 604 to connect the ring of frame cells 802 to the support wire 106. The branch geometry can transmit forces, e.g., pulling forces, to the expandable frames 604 during operation, and can contribute to clot capture.

With respect to pull force transmission, the branches can bifurcate once or more between the proximal stem end 804 and the proximal frame end 708 to form a structure that connects to each of the proximal ring ends 803. More particularly, the stem 602 can extend proximally from each proximal apex of the expandable ring structure, and thus, pull forces transmitted from the support wire 106 to the expandable frame 604 though the stem branches will be uniformly distributed around the proximal frame end 708. The uniform distribution of pull force can reduce tilting of the expandable frame 604 during device retrieval, and thus, may reduce vessel injury and or clot loss.

Several of the branches of the stem 602 can define a mouth 810 to an interior channel 812 of the expandable frame 604. For example, a pair of branches can bifurcate near the proximal stem end 804 and extend distally toward the proximal ring end 803. At the proximal ring end 803, the pair of branches can continue along a proximal edge of the ring of frame cells 802 to converge at a link 820 between two adjacent frame cells. The diverging and converging branches can form an eye-shaped mouth 810 that provides a proximal opening into the interior channel 812. More particularly, the negative space between the two arcuate branches can provide the mouth 810. Likewise, another mouth can be defined between branches of the stem 602 on an opposite side of the arrestor structure. The other mouth can be separated from the illustrated mouth 810 by the branches, but can open into the same interior channel 812. Accordingly, the mouths of the clot arrestor 108 provide ports through which clots can enter into and be captured by the expandable frame 604.

Figure 9:
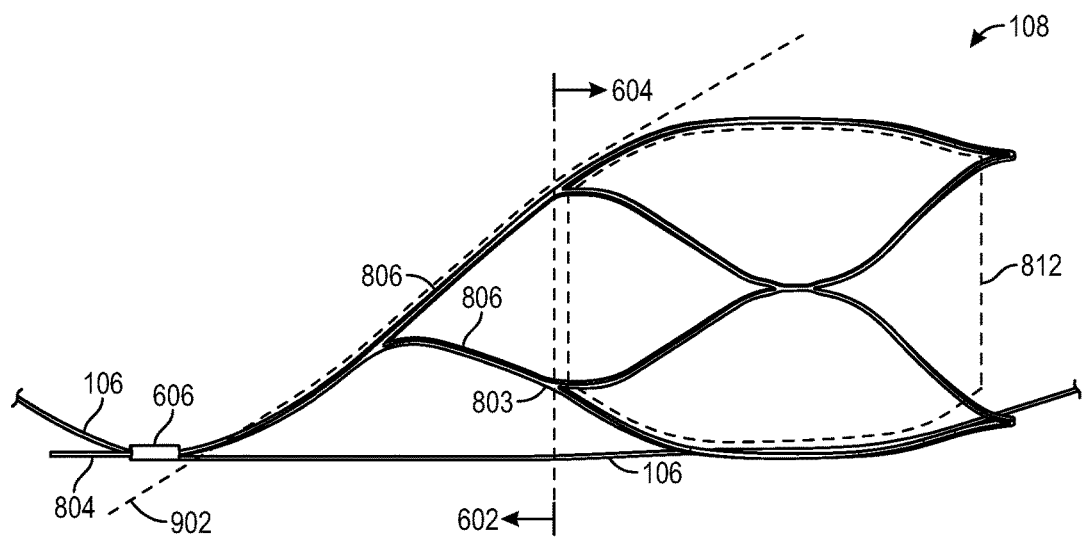
FIG. 9 is a side view of a clot arrestor, in accordance with an embodiment.

Referring to FIG. 9, a side view of a clot arrestor is shown in accordance with an embodiment. In the side view, the division between the expandable frame 604 distal to the proximal ring end 803 and the stem 602 proximal to the proximal ring end 803 is seen. The interior channel 812 is the volume within the expandable frame 604. The stem 602 extends proximally from the expandable frame 604 to the joint 606 at the proximal stem end 804, which joins the clot arrestor 108 to the support wire 106. The branches of the stem 602 can bifurcate to connect to different proximal ring ends 803. Furthermore, the branches form the mouth 810, which in the side view, has a mouth plane 902. The mouth plane 902 is the plane containing the negative space between the branches that define the mouth 810, as described above. In an embodiment, the mouth plane 902 extends transverse to the support wire 106. For example, whereas the support wire 106 includes the wire axis extending in the longitudinal direction, the mouth plane 902 may be arranged oblique to the wire axis, neither parallel nor perpendicular to the wire.

The angle of the mouth plane 902 relative to the wire axis 402, e.g., the oblique angle, can promote clot capture. For example, by angling the mouth plane 902 it can provide a laterally directed opening through which a clot can more easily pass. The oblique angle is one factor affecting a size of the gap 704 between adjacent expandable frames 604. As described above, the size can impact the type of clot that is captured and how easily the clot is captured. For example, the angled mouth plane 902 can provide a more generous lead-in to the interior channel 812 to allow hard clots to roll more easily into the interior channel 812.

Figure 10:
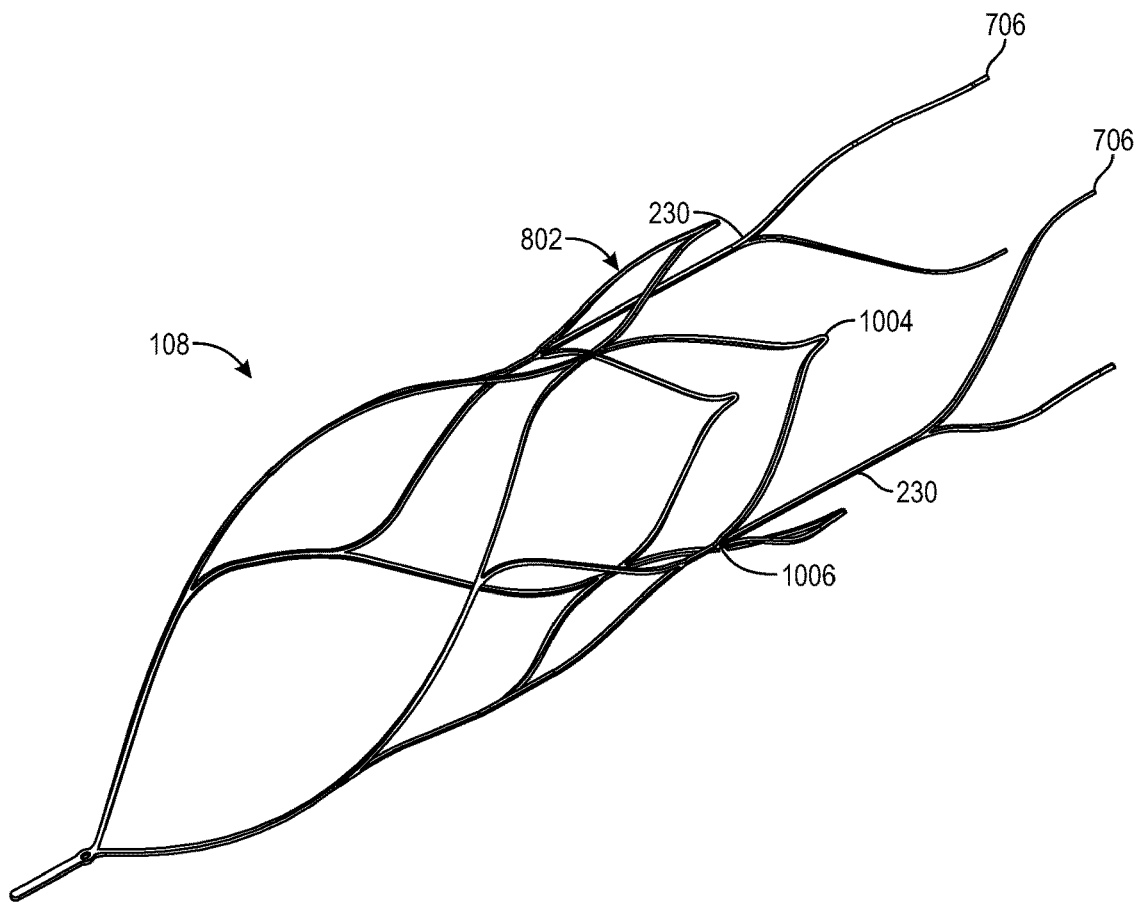
FIG. 10 is a perspective view of a clot arrestor, in accordance with an embodiment.

Referring to FIG. 10, a perspective view of a clot arrestor is shown in accordance with an embodiment. As described above, the clot arrestors 108 of the mechanical thrombectomy device 100 can have varied geometries. In an embodiment, one or more of the expandable frames 604 includes several struts 230 extending distal to the ring of frame cells 802. The struts 230 can extend distally from an the distal edge of the ring of frame cells 802. For example, the struts 230 can extend from an apex 1004 or a trough 1006 of the cell pattern at the distal edge. The struts 230 can bifurcate, as shown, to extend to several terminal ends at the distal frame end 706. Alternatively, the struts 230 may be unitary segments, e.g., straight strut protrusions that have a single proximal end at the ring of frame cells 802 and a single distal end at the distal frame end 706.

Figure 11:
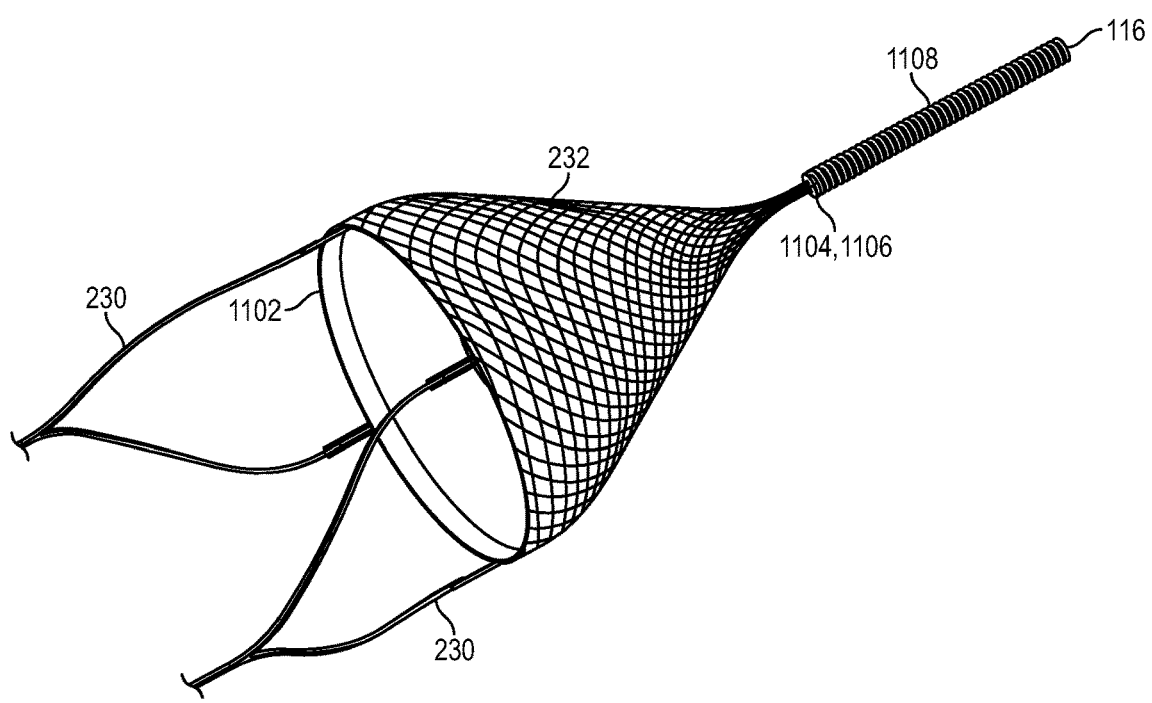
FIG. 11 is a perspective view of a filter mounted on a clot arrestor, in accordance with embodiment.

Referring to FIG. 11, a perspective view of a filter mounted on a clot arrestor is shown in accordance with embodiment. The mechanical thrombectomy device 100 can include a filter 232 to capture clots that pass distal to the expandable frames 604. In an embodiment, the filter 232 is coupled to the ring of frame cells 802. For example, the filter 232 can be mounted on the struts 230 that extend distally from the ring of frame cells 802. The filter 232 can have a distally converging geometry. More particularly, the filter 232 can extend distally from a proximal filter end 1102 to a distal filter end 1104, and the proximal filter end 1102 can have a larger transverse dimension than the distal filter end 1104. The converging geometry can form a closed structure to traverse a lumen of the blood vessel 502 and capture any clots or portions of clots that pass distal to the expandable frames 604.

In an embodiment, the filter 232 includes a mesh structure. For example, the filter 232 can be formed from a polymer or metal filament that is braided into a mesh having a distally-converging structure, such as a conical shape. The mesh can have a porosity that allows blood to pass, but captures clots or portions of clots that flow distal to the expandable frames 604. In an embodiment, the mesh is formed from a shape-memory material, such as a nickel titanium alloy, however, the filter 232 may alternatively be formed from another material or metal, such as stainless steel.

Figure 16:
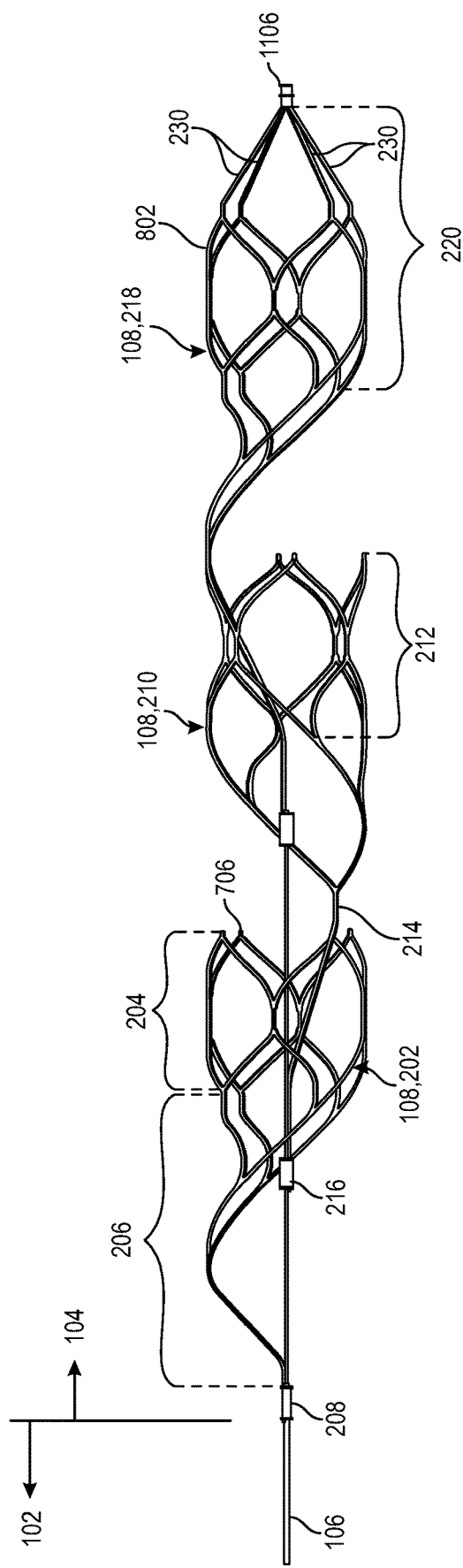
FIG. 16 is a plan view of a distal portion of a mechanical thrombectomy device having several clot arrestors, in accordance with an embodiment.

The filter 232 may be formed from a thin sheet of material having a predetermined porosity. For example, the filter 232 may be formed from a polymer film having one or more holes formed through the film to permit blood flow. The filter 232 can be freely suspended at the proximal filter end 1102. More particularly, there may be no internal framing to support the filter 232. Alternatively, the filter 232 can be supported by one or more of the struts 230 extending distally from the expandable frame 604. In an embodiment, the struts 230 converge to a point (FIG. 16). The freely suspended and/or internally supported filter 232 can collapse during device delivery and expand within the target anatomy to protect against the distal migration of clots.

The clot arrestor 108 can include a coil tip 1108. The coil tip 1108 can extend distally from the filter 232. The coil tip 1108 can be flexible and atraumatic to the vessel wall 504. The coil tip 1108 can be radiopaque to provide improved visibility of the distal end of the clot arrestor 108. For example, the coil tip 1108 can be formed from stainless steel, platinum-iridium, or another radiopaque metal or material that is visible under fluoroscopy. In an embodiment, the coil tip 1108 is joined to the filter 232 and/or struts 230 of the expandable frame 604 by a mechanical, thermal, or adhesive joint. For example, the joint can be an adhesive joint, which bonds the filter 232 to the coil tip 1108.

Whereas the filter 232 is shown as being a portion of the distalmost clot arrestor 108 (e.g., FIG. 2), it will be appreciated that any of the clot arrestors 108 of the mechanical thrombectomy device 100 can include a respective filter 232. Furthermore, any of the clot arrestors 108 (proximalmost, medial, distalmost, etc.) can have distal ends that converge to respective distal tips 1106. More particularly, any and all of the expandable frames 604 can be enclosed at their distal ends to provide a cage-like or filter-like structure that captures distally moving clots. As with any of the clot arrestor structures described herein, the distal geometry of the clot arrestors can be the same or different for each clot arrestor relative to another clot arrestor.

Figure 12:
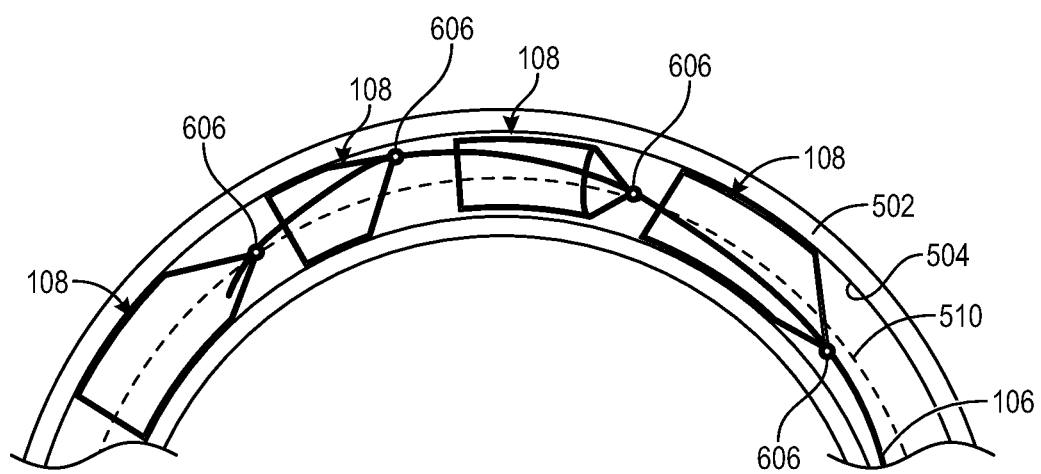
FIG. 12 is a pictorial view of a mechanical thrombectomy device deployed in a curved vessel, in accordance with embodiment.

Referring to FIG. 12, a pictorial view of a mechanical thrombectomy device deployed in a curved vessel is shown in accordance with embodiment. The view provides a visual depiction of an advantage of the eccentrically supported expandable frames 604 and undulating support wire 106, as described above. When the mechanical thrombectomy device 100 is deployed in the blood vessel 502, each clot arrestor 108 can be attached to the support wire 106 at a joint 606 that has a stem extending from the joint with a different clocking, relative to the central axis 510 of the blood vessel 502. For example, in the embodiment shown, the mechanical thrombectomy device 100 can have four clot arrestors 108, each with respective joints 606 and stems having clocking that differs by 90-degrees relative to an adjacent stem. More particularly, the proximalmost clot arrestor 108 can have a stem at a zero-degree position relative to the central axis 510 (at a bottom position of the vessel wall 504), a second clot arrestor 210 adjacent to the proximalmost clot arrestor 108 can have a joint 606 at a 90-degree position (measured counterclockwise about the central axis 510), a third clot arrestor 218 adjacent to the second clot arrestor 210 can have a stem at a 180-degree position, and a distalmost clot arrestor 108 adjacent to the third clot arrestor 218 can have a stem at a 270-degree position. As described above, the distal segment 304 of the support wire 106 can undulate or spiral along and/or about the central axis 510 to connect to the clot arrestors 108 at the joints 606. More particularly, the support wire 106 can press against the vessel wall 504 at each of the joint locations at alternately clocked locations relative to the central axis 510. Accordingly, the support wire 106 can extend through the expandable frames 604 offset from the central axis 510 of the blood vessel 502. The offset location opens the central lumen of the blood vessel 502 and the interior channels 812 of the expandable frames 604 to allow clots to move through the gaps 704 between clot arrestors 108 into the interior channels 812 for capture.

Figure 13:
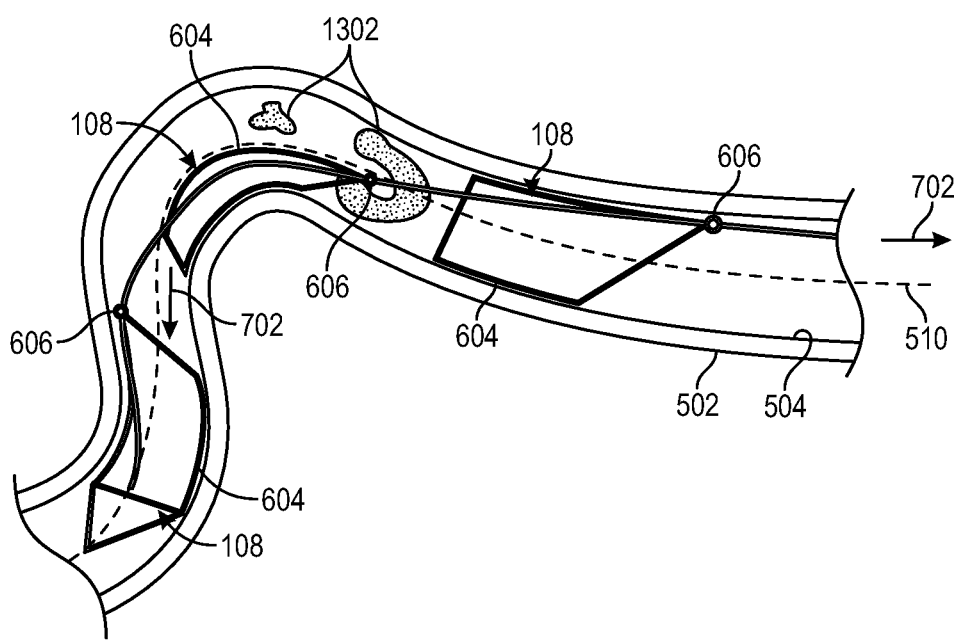
FIG. 13 is a pictorial view of a mechanical thrombectomy device being retracted around a bend in a tortuous blood vessel, in accordance with an embodiment.

Referring to FIG. 13, a pictorial view of a mechanical thrombectomy device being retracted around a bend in a tortuous blood vessel is shown in accordance with an embodiment. The view provides a visual depiction of an advantage of the independently mounted clot arrestors 108, as described above. The expandable frames 604 are connected to the support wire 106, but are not directly coupled to each other. Thus, the independently supported clot arrestors 108 are afforded a degree of freedom relative to each other, which leads to localized deformation of individual expandable frames 604 without global deformation of one or more other expandable frames 604. That is, the deformation of one expandable frame 604 does not necessarily impact the other expandable frames 604.

In an embodiment, when the mechanical thrombectomy device 100 is deployed into a tortuous blood vessel 502, one or more of the clot arrestors 108 may be retracted over a bend in the vessel. More particularly, the support wire 106 is retracted through the blood vessel 502 to retrieve the clot arrestors 108 (and any clots captured by the clot arrestors). Retraction of the support wire 106 can cause a deforming load 702 to be applied to one of the expandable frames 604. As described above, the deforming load 702 can have a radial component in some cases, and in the case of retracting over the bend, the deforming load 702 can also have an axial component that causes the expandable frame 604 located at the bend to stretch. More particularly, the tension caused by a proximal load applied to the joint 606 of the deformed clot arrestor 108 and a distal load applied by drag against the vessel wall 504 can stretch the clot arrestor 108, as shown in FIG. 13. The deforming load 702 can cause the stretched expandable frames 604 to lengthen and, concomitantly, to reduce in diameter. As a result of the reducing diameter, the expandable frame 604 can lose apposition with the vessel wall 504. The other clot arrestors 108, however, are independently mounted on the support wire 106 and can therefore remain unstretched despite the stretching of the clot arrestor 108 at the bend. The other clot arrestors 108, accordingly, do not lose apposition with the vessel wall 504. Accordingly, deformation of the clot arrestors 108 is localized (and minimized) to the clot arrestor 108 at the bend, while ensuring 802 that the blood vessel 502 proximal and distal to the bend remains protected by adjacent clot arrestors 108. As a result, any clot 1302 that is force out of the stretched clot arrestor 108 or which breaks away and flows downstream within the vessel lumen can be captured by an adjacent clot arrestor 108. A likelihood of capturing an entire clot 1302 and retrieving the thrombus from the target anatomy is therefore increased by the independently mounted clot arrestors 108.

Figure 14:
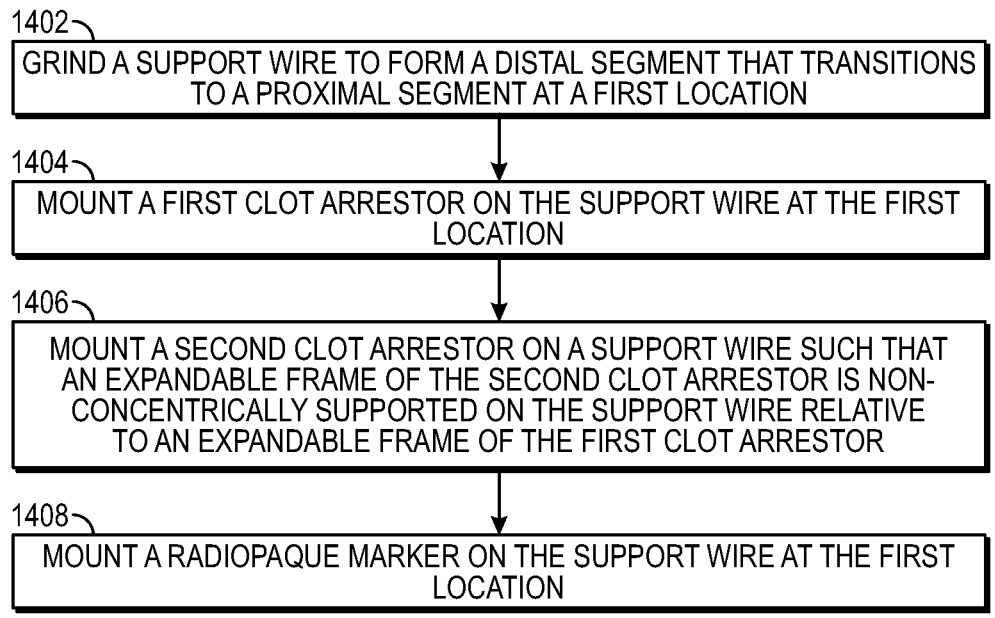
FIG. 14 is a flowchart of a method of manufacturing a mechanical thrombectomy device, in accordance with an embodiment.

Referring to FIG. 14, a flowchart of a method of manufacturing a mechanical thrombectomy device is shown in accordance with an embodiment. The method described below is provided by way of example, and those skilled in the art would understand that such a method could be performed using alternative and/or additional manufacturing operations to provide the mechanical thrombectomy device 100 described above.

At operation 1402, the support wire 106 is formed. In an embodiment, the support wire 106 is formed by grinding the a wire, e.g., a shape memory alloy wire, to form a distal segment 304 that transitions to a proximal segment 302 at the first location 209. As described above, the support wire 106 can include several transitions to provide a wire that tapers in a continuous or step-wise fashion from the proximal wire end 110 to the distal wire end 112. For example, the distal segment 304 can have a smaller diameter than the proximal segment 302. Accordingly, the support wire 106 can have a stiffness profile that decreases in the distal direction.

In an embodiment, rather than (or in addition to) grinding the support wire 106, the support wire 106 can be formed from several wire segments that are joined at discrete locations. The wire segments can be joined using mechanical, thermal, or adhesive joints 606. A distal wire segment can have a smaller diameter than a proximal wire segment to provide the decreasing stiffness profile in the distal direction.

At operation 1404, a first clot arrestor 202 is mounted on the support wire 106 at the first location 209. The first clot arrestor 202 can be attached to the support wire 106 by a mechanical, thermal, or adhesive joint 606, such as the crimped marker band embedded in an adhesive bond, as described above. When attaching the first clot arrestor 202, the clot arrestor 108 can be oriented such that the stem 602 of the first clot arrestor 202 extends from the support wire 106 at a first circumferential location, e.g., a first clocking, relative to the wire axis 402. The clocking can cause the first clot arrestor 202 to have a radial plane that extends through the wire axis 402 and the arrestor axis 416 in a first radial direction.

At operation 1406, a second clot arrestor 210 is mounted on the support wire 106 at a second location 217. The second clot arrestor 210 can be attached to the support wire 106 by a mechanical, thermal, or adhesive joint 606, such as the crimped marker band embedded in an adhesive bond, as described above. The second location 217 can be longitudinally offset from the first location 209, and may be distal to or proximal to the expandable frame 604 of the first clot arrestor 202. When attaching the second clot arrestor 210, the clot arrestor 108 can be oriented such that the stem 602 of the second clot arrestor 210 extends from the support wire 106 at a second circumferential location, e.g., a second clocking, different than the first circumferential location. The clocking can cause the second clot arrestor 210 to have a radial plane that extends through the wire axis 402 and the arrestor axis 416 in a second radial direction that is circumferentially offset from the first radial direction. Accordingly, the first and second clot arrestors 202, 210 can be independently and eccentrically mounted on the support wire 106. Furthermore, the expandable frames 604 can be non-concentrically supported on the support wire 106 relative to each other.

At operation 1408, a radiopaque marker 310 is mounted on the support wire 106 at the first location 209 and/or the second location 217. The radiopaque marker 310 can mechanically join the stem 602 of the expandable frame 604 to the support wire 106. For example, the radiopaque marker 310 can be a marker band that is crimped around the stem 602 and the support wire 106. Alternatively, the radiopaque marker 310 can be a radiopaque particle, ink, or other structure that is joined to the support wire 106 by an adhesive to provide visibility of the joint 606 for positional feedback to an operator.

Figure 15:
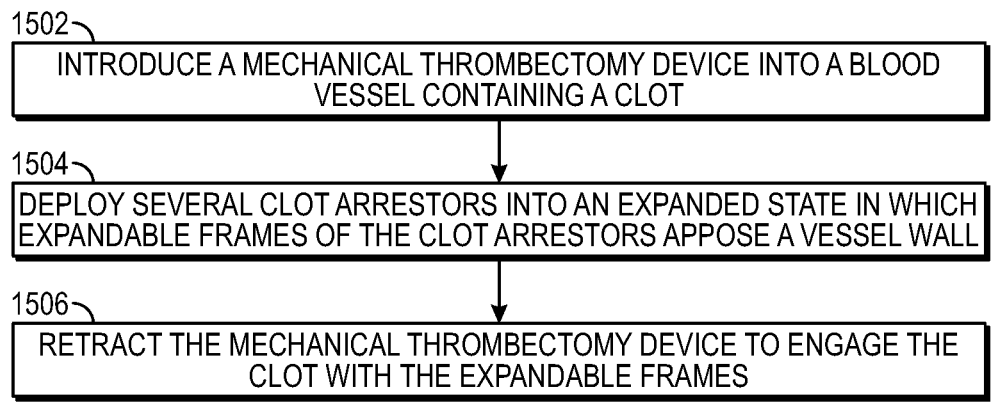
FIG. 15 is a flowchart of a method of removing a clot from a blood vessel using a mechanical thrombectomy device, in accordance with an embodiment.

Referring to FIG. 15, a flowchart of a method of removing a clot from a blood vessel using a mechanical thrombectomy device is shown in accordance with an embodiment. At operation 1502, a mechanical thrombectomy device 100 is introduced into a blood vessel 502 containing a clot 1302. Initially, a guide wire can be traversed through the blood vessel 502 into a targeted area in a narrow vasculature that is at least partially blocked by the clot 1302. A microcatheter can be tracked over the guidewire such that a distal end of the microcatheter is located distal to the clot 1302. The guidewire can be retracted and removed from the microcatheter when the microcatheter is in place. The mechanical thrombectomy device 100 can then be advanced through a lumen of the microcatheter until the distal tip 1106 of the mechanical thrombectomy device 100 is located near or distal to the distal end of the microcatheter. When the mechanical thrombectomy device 100 is introduced into the blood vessel 502, the microcatheter can maintain the clot arrestors 108 in a constrained configuration. That is, the microcatheter lumen may have a smaller diameter than the expanded clot arrestors 108, and thus, the expandable frames 604 can be introduced into the blood vessel 502 through the microcatheter in an unexpanded state.

At operation 1504, the clot arrestors 108 are deployed. Forward pressure can be placed on the support wire 106 of the mechanical thrombectomy device 100 while retracting the microcatheter to cause the clot arrestors 108 to deploy from the distal end of the microcatheter into apposition with the vessel wall 504 of the blood vessel 502. More particularly, the expandable frames 604 can transition into an expanded state (FIG. 1). In the expanded state, the expandable frames 604 appose the vessel wall 504. The expandable frames 604 are eccentrically supported on the support wire 106, and thus, when the expandable frames 604 are deformed into a concentric arrangement within the vessel (FIG. 12), the expandable frames 604 press against the vessel wall 504 in different transverse directions. The non-concentrically supported expandable frames 604, when biased into alignment, also cause the support wire 106 to be biased off-center and toward the vessel wall 504. More particularly, the support wire 106 extends through the blood vessel 502 offset from the central axis 510 of the blood vessel 502.

After expanding the clot arrestors 108, the mechanical thrombectomy device 100 may be left in place for several minutes to allow the expandable frames 604 to engage the clot 1302. At operation 1506, the support wire 106 can then be pulled to retract the mechanical thrombectomy device 100 to further engage, arrest, or capture the clot 1302 with the expandable frames 604. The support wire 106 can be pulled until the clot arrestors 108, and the captured clot 1302, are removed from the target vasculature.

Referring to FIG. 16, a plan view of a distal portion of a mechanical thrombectomy device having several clot arrestors is shown in accordance with an embodiment. The distal working region 104 of the mechanical thrombectomy device 100 can include several features that are interchangeable with the embodiments described above. Such features are not repeated with respect to FIG. 16 in the interest of brevity.

In an embodiment, the distal working region 104 includes several clot arrestors 108 having expandable frames 604 arranged sequentially in the longitudinal direction. For example, the second expandable frame 212 can be distal to the first expandable frame 204. Similarly, the third expandable frame 220 can be distal to the second expandable frame 212. In the embodiment illustrated in FIG. 2, the clot arrestors 108 are arranged in a non-overlapping fashion, with each joint 606 of a clot arrestor 108 being located distal to an immediately proximal clot arrestor 108. As shown in FIG. 16, the clot arrestors 108 may, however, be at least partly overlapping in the longitudinal direction. For example, the second clot arrestor 210 can include a second stem 214 that is coupled to the support wire 106 at a location that is proximal to the distal frame end 706 of the first expandable frame 204. More particularly, the second stem 214 can be attached to the support wire 106 at the second joint 216, which is proximal to the first expandable frame 204.

The overlapping clot arrestors 108 can be facilitated by the elongated stems 602 that extend proximally from a more distal expandable frame 604 to the support wire 106 at a location proximal to a more proximal expandable frame 604. The elongated stem 602 can provide increased flexibility and movement of the expandable frame 604 relative to the support wire 106. Accordingly, although the expandable frames 604 are shown as being concentrically arranged along the support wire 106, it will be appreciated that the expandable frames 604 could hinge outward at the joints 606 to cause the expandable frames 604 to be non-concentrically (and eccentrically) supported on the support wire 106 (FIG. 17).

In addition to making the expandable frames 604 more resilient and flexible about the support wire 106, connecting the expandable frames 604 at joints 606 that are outside of the interior channel 812 of an adjacent expandable frame 604 can contribute to optimal packing ratio of the mechanical thrombectomy device 100. As described above, by placing the joints 606 at locations along the support wire 106 that are not radially inward from the ring of frame cells 802 can allow the ring of frame cells 802 can be compacted to a smaller dimension during delivery. Thus, placement of the joints 606 proximal to the expandable frames 604 can improve deliverability of the device.

Still referring to FIG. 16, one or more of the clot arrestors 108 of the mechanical thrombectomy device 100 can have enclosed distal ends. For example, the third clot arrestor 218 (the distalmost clot arrestor) can include several struts 230 protruding distally from the ring of frame cells 802. The struts 230 can converge at the distal tip 1106 to form an enclosed cage-like structure. More particularly, the cage-like structure formed from struts 230 defines an outline of a funnel or conical shape that can allow blood flow but can also provide some resistance to the distal flow of the clot 1302 through the blood vessel 502.

Figure 17:
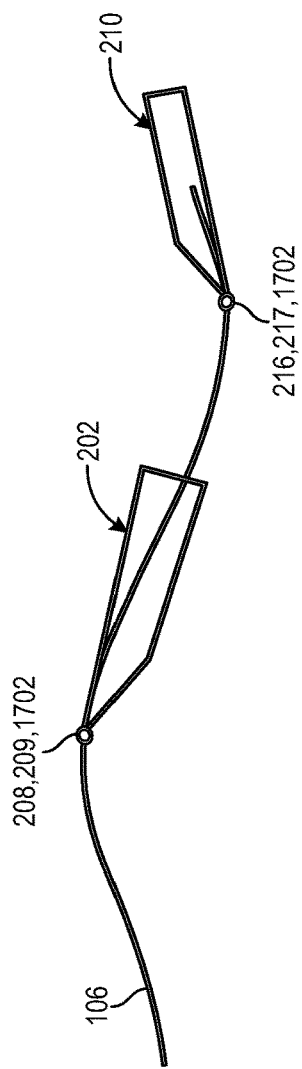
FIG. 17 is a pictorial view of a mechanical thrombectomy device including a support wire having one or more inflections, in accordance with an embodiment.

Referring to FIG. 17, a pictorial view of a mechanical thrombectomy device including a support wire having one or more inflections is shown in accordance with an embodiment. The undulating and/or spiraling distal segment 304 of the support wire 106 can include one or more inflections 1702. Each inflection 1702 can be a change in a curvature of the support wire 106 along the wire axis 402 in the distal direction. The inflections 1702 can coincide with locations at which the clot arrestors 108 are mounted on the support wire 106. For example, an undulation may be a peak along which the first location 209 is located. The first location 209 can be the location at which the first joint 208 connects the first clot arrestor 202 to the support wire 106. Similarly, an undulation may be a trough 1006, immediately distal to the peak, along which the second location 217 is located. The second location 217 can be the location at which the second joint 216 connects the second clot arrestor 210 to the support wire 106.

The inflections 1702 along the support wire 106 can be caused by the interaction between the clot arrestors 108 and the vessel wall 504. For example, the spiraling path of the support wire 106 described above can pass through the joints 606, and thus, the inflections 1702 may be caused by the support wire 106 taking a particular shape to extend from one joint 606 to another. Alternatively, the inflections 1702 may be caused directly by the clot arrestors 108 themselves. For example, the clot arrestors 108 may have a stem hole 1704 (FIG. 8) passing through the stem 602, e.g., near the proximal stem end 804. The support wire 106 may be threaded through the stem hole 1704 (FIG. 9), and in doing so, an angle may be naturally created between the stem 602 at the stem hole 1704 and the support wire 106 at the stem hole 1704. Furthermore, when the joint 606 is formed by crimping a marker band around the support wire 106 and the stem 602, the joint 606 can cause a localized bending moment in the support wire 106 at the stem hole 1704. The bending moment can produce a bend, which causes the inflection 1702 to be located at the joint 606. Accordingly, the mechanical thrombectomy device 100 can have a support wire 106 which, when deployed in free space or within the blood vessel 502, has an inflection 1702 for each of the clot arrestors 108 mounted on the distal segment 304.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A mechanical thrombectomy device, comprising:
 a support wire; and
 a plurality of clot arrestors independently mounted on the support wire, wherein each clot arrestor includes an expandable frame having a circular-cross-sectional profile, wherein the support wire extends through one or more of the expandable frames, and wherein, when the plurality of clot arrestors are deployed in free space, the circular cross-sectional profiles are arranged eccentrically relative to the support wire and non-concentrically relative to each other such that, when the plurality of clot arrestors are deployed in a blood vessel with the expandable frames apposed to a vessel wall, the expandable frames are forced into a concentric relationship with the vessel wall and the support wire is forced to undulate along the vessel wall offset from a central axis of the blood vessel.

2. The mechanical thrombectomy device of claim 1, wherein the expandable frames are non-concentrically supported on the support wire relative to each other such that, when the plurality of clot arrestors are deployed in the blood vessel, the expandable frames press against the vessel wall in different transverse directions.

3. The mechanical thrombectomy device of claim 1, wherein the support wire spirals along the vessel wall when the expandable frames are apposed to the vessel wall.

4. The mechanical thrombectomy device of claim 1, wherein each clot arrestor includes a stem coupling the expandable frame to the support wire at a joint, and wherein the joints are spaced longitudinally along the support wire such that a deforming load applied to one of the expandable frames is not transmitted to another one of the expandable frames.

5. The mechanical thrombectomy device of claim 4, wherein the deforming load is caused by retracting the support wire through the blood vessel, and wherein the plurality of clot arrestors are independently mounted such that the deforming load causes the one of the expandable frames to stretch or lose apposition with the vessel wall while the another one of the expandable frames does not stretch or lose apposition with the vessel wall.

6. The mechanical thrombectomy device of claim 4, wherein the plurality of clot arrestors include a first clot arrestor having a first expandable frame and a first stem, and a second clot arrestor having a second expandable frame and a second stem, wherein the second expandable frame is distal to the first expandable frame, and wherein the second stem is coupled to the support wire at a respective joint proximal to the first expandable frame.

7. The mechanical thrombectomy device of claim 4 further comprising a radiopaque marker at the joint.

8. The mechanical thrombectomy device of claim 4, wherein each clot arrestor has a respective line passing through a respective arrestor axis and a wire axis of the support wire, and wherein the lines are angularly offset from each other about the wire axis of the support wire.

9. The mechanical thrombectomy device of claim 8, wherein the respective lines are uniformly distributed about the support wire.

10. The mechanical thrombectomy device of claim 4, wherein each of the expandable frames include a ring of frame cells coupled to the stem.

11. The mechanical thrombectomy device of claim 10, wherein the stem includes a plurality of branches, and wherein the plurality of branches extend between the joint and a proximal ring end of the ring of frame cells to define a mouth to an interior channel of the expandable frame.

12. The mechanical thrombectomy device of claim 11, wherein the mouth has a mouth plane extending transverse to the support wire.

13. The mechanical thrombectomy device of claim 10, wherein one or more of the expandable frames includes a plurality of struts extending distal to the ring of frame cells to converge at a distal tip.

14. The mechanical thrombectomy device of claim 10 further comprising a filter coupled to the ring of frame cells.

15. The mechanical thrombectomy device of claim 1, wherein the support wire includes a proximal segment proximal to the plurality of clot arrestors, and a distal segment extending through one or more of the plurality of clot arrestors, wherein the proximal segment is linear, and wherein the distal segment is non-linear.

16. The mechanical thrombectomy device of claim 15, wherein the distal segment includes one or more inflections.

17. The mechanical thrombectomy device of claim 16, wherein the one or more inflections coincide with locations at which the plurality of clot arrestors are mounted on the support wire.

18. The mechanical thrombectomy device of claim 15, wherein the proximal segment of the support wire has a larger diameter than the distal segment of the support wire.

19. A method of removing a clot from a blood vessel, comprising:
   introducing a mechanical thrombectomy device into the blood vessel containing the clot, wherein the mechanical thrombectomy device includes a support wire and a plurality of clot arrestors independently mounted on the support wire, and wherein each clot arrestor includes an expandable frame having a circular-cross-sectional profile, wherein the support wire extends through one or more of the expandable frames, wherein, when the plurality of clot arrestors are deployed into an expanded state in free space, the circular cross-sectional profiles are arranged eccentrically relative to the support wire and non-concentrically relative to each other, and wherein the expandable frames are introduced into the blood vessel in an unexpanded state;
   deploying the plurality of clot arrestors to transition the expandable frames into the expanded state in the blood vessel such that the expandable frames appose a vessel wall, wherein the expandable frames are forced into a concentric relationship with the vessel wall and the support wire is forced to undulate along the vessel wall offset from a central axis of the blood vessel; and
   retracting the mechanical thrombectomy device to engage the clot with the expandable frames.

20. A mechanical thrombectomy device, comprising:
   a support wire; and
   a plurality of clot arrestors independently mounted on the support wire, wherein each clot arrestor includes an expandable frame eccentrically supported on the support wire such that, when the plurality of clot arrestors are deployed in a blood vessel with the expandable frames apposed to a vessel wall, the support wire extends through one or more of the expandable frames offset from a central axis of the blood vessel, and wherein the support wire spirals along the vessel wall when the expandable frames are apposed to the vessel wall.

21. A mechanical thrombectomy device, comprising:
   a support wire; and
   a plurality of clot arrestors independently mounted on the support wire, wherein each clot arrestor includes an expandable frame eccentrically supported on the support wire such that, when the plurality of clot arrestors are deployed in a blood vessel with the expandable frames apposed to a vessel wall, the support wire extends through one or more of the expandable frames offset from a central axis of the blood vessel, wherein the support wire includes a proximal segment proximal to the plurality of clot arrestors, and a distal segment extending through one or more of the plurality of clot arrestors, wherein the proximal segment is linear, and wherein the distal segment is non-linear.

22. The mechanical thrombectomy device of claim 21, wherein the distal segment includes one or more inflections.

23. The mechanical thrombectomy device of claim 22, wherein the one or more inflections coincide with locations at which the plurality of clot arrestors are mounted on the support wire.

24. The mechanical thrombectomy device of claim 21, wherein the proximal segment of the support wire has a larger diameter than the distal segment of the support wire.

* * * * *